(12) United States Patent
Ichimura

(10) Patent No.: US 8,394,013 B2
(45) Date of Patent: Mar. 12, 2013

(54) ENDOSCOPE

(75) Inventor: Hironobu Ichimura, Akishima (JP)

(73) Assignee: Olympus Medical Systems Corp. (JP)

( * ) Notice: Subject to any disclaimer, the term of this patent is extended or adjusted under 35 U.S.C. 154(b) by 668 days.

(21) Appl. No.: 12/333,666

(22) Filed: Dec. 12, 2008

(65) Prior Publication Data
US 2009/0093681 A1    Apr. 9, 2009

Related U.S. Application Data

(63) Continuation of application No. PCT/JP2007/062120, filed on Jun. 15, 2007.

(30) Foreign Application Priority Data

Jun. 15, 2006 (JP) .................................. 2006-166176

(51) Int. Cl.
*A61B 1/04* (2006.01)
*A61B 1/00* (2006.01)
*A61B 1/12* (2006.01)
*A61B 1/06* (2006.01)

(52) U.S. Cl. ...................... 600/129; 600/157; 600/167

(58) Field of Classification Search .................. 600/129, 600/164, 165, 171, 156, 157, 160, 175, 176, 600/166

See application file for complete search history.

(56) References Cited

U.S. PATENT DOCUMENTS

| | | | | | |
|---|---|---|---|---|---|
| 5,325,847 | A | * | 7/1994 | Matsuno | 600/109 |
| 5,746,695 | A | * | 5/1998 | Yasui et al. | 600/127 |
| 5,916,148 | A | | 6/1999 | Tsuyuki | |
| 6,142,932 | A | * | 11/2000 | Morizumi | 600/166 |
| 7,267,647 | B2 | * | 9/2007 | Okada et al. | 600/166 |
| 7,914,447 | B2 | * | 3/2011 | Kanai | 600/160 |
| 2003/0040657 | A1 | | 2/2003 | Yamaya et al. | |
| 2004/0158129 | A1 | | 8/2004 | Okada et al. | |
| 2004/0242963 | A1 | * | 12/2004 | Matsumoto et al. | 600/127 |
| 2005/0052753 | A1 | * | 3/2005 | Kanai | 359/642 |

FOREIGN PATENT DOCUMENTS

| | | |
|---|---|---|
| JP | 3-56402 | 5/1991 |
| JP | 2002-238835 | 8/2002 |
| JP | 2005-640 | 1/2005 |
| JP | 2005-13708 | 1/2005 |

OTHER PUBLICATIONS

English translation of International Preliminary Report on Patentability mailed Dec. 31, 2008 in corresponding PCT International Application No. PCT/JP2007/062120.
Letter from German associate dated May 19, 2009 forwarding the Search Report dated May 11, 2009 to Japanese associate, including discussion of relevancy thereof.
Search Report issued by European Patent Office in connection with corresponding application No. EP 07 74 5375 on May 11, 2009.
International Search Report mailed Sep. 11, 2007 in corresponding PCT International Application No. PCT/JP2007/062120.

* cited by examiner

*Primary Examiner* — Alireza Nia
(74) *Attorney, Agent, or Firm* — Ostrolenk Faber LLP

(57) ABSTRACT

The present invention has a configuration that an observing portion observing an area to be examined and first and second illumination portions performing irradiation of illumination light are disposed on a distal end face of an insertion portion to be inserted into the area to be examined, and a first lens which is a distal end observation lens of an observation window of the observation portion is disposed at a position projecting to a distal end side beyond the distal end face. With the abovementioned configuration, an endoscope provided with an observation optical system of an object contact type performing contact observation to a live body where a sharp observation image can be obtained is provided.

5 Claims, 12 Drawing Sheets

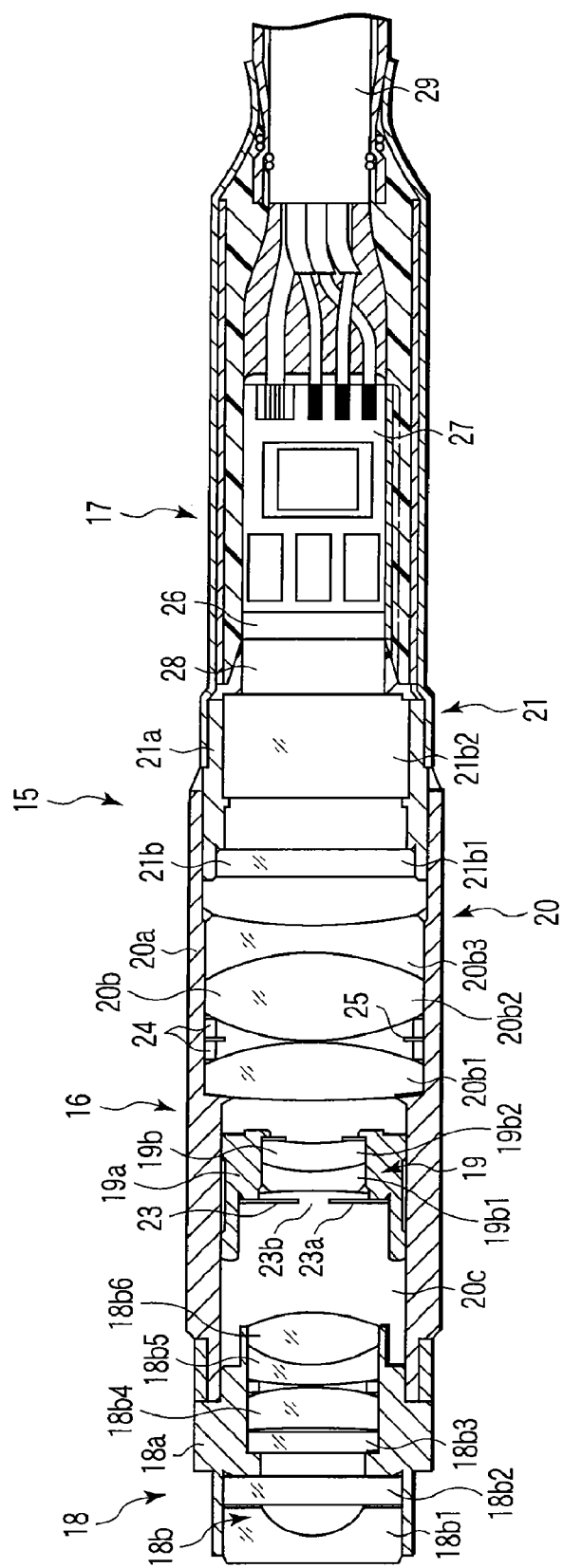
F I G. 3

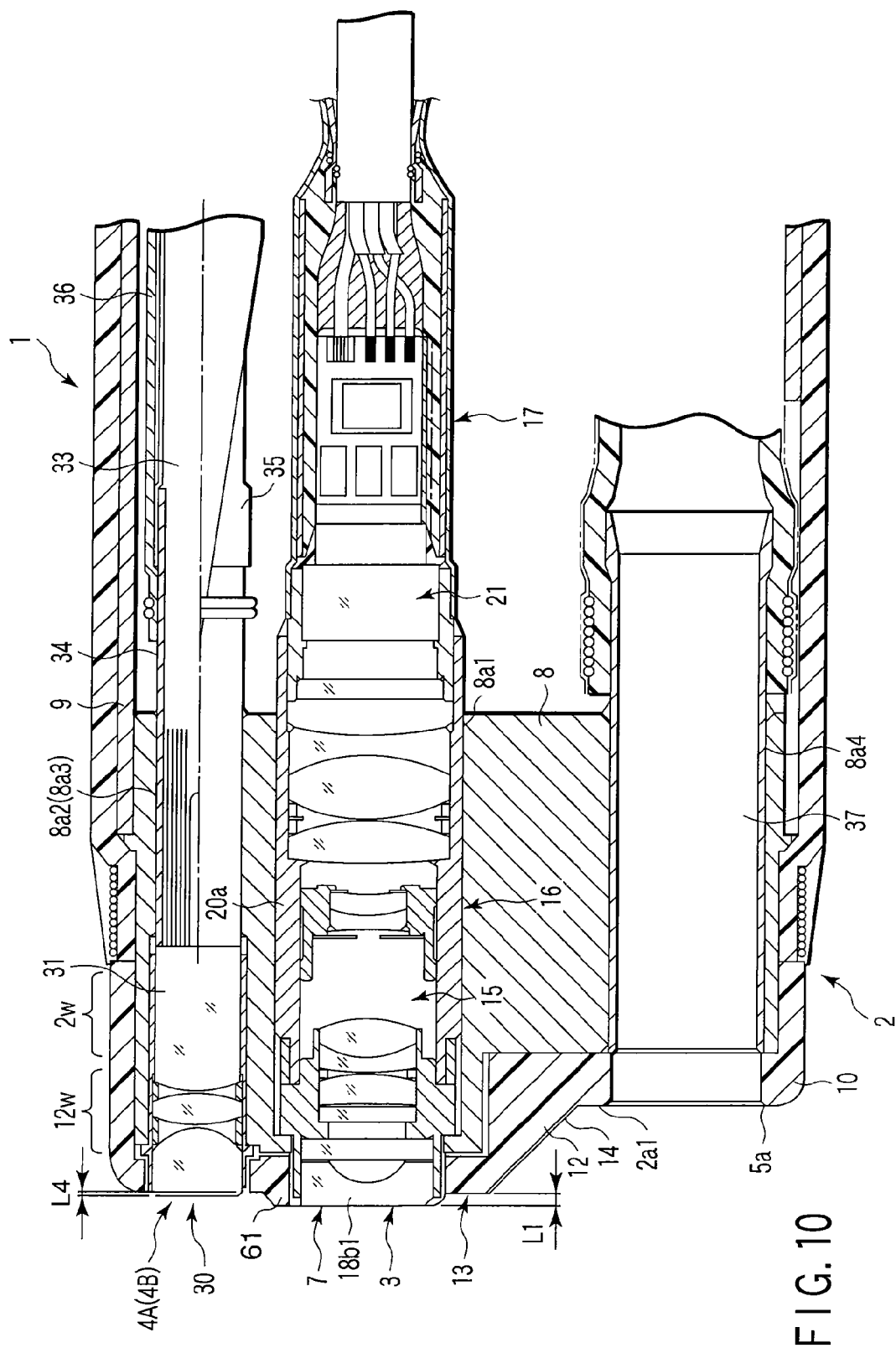
F I G. 10

ENDOSCOPE

CROSS REFERENCE TO RELATED APPLICATIONS

This is a Continuation Application of PCT Application No. PCT/JP2007/062120, filed Jun. 15, 2007, which was published under PCT Article 21(2) in Japanese.

This application is based upon and claims the benefit of priority from prior Japanese Patent Application No. 2006-166176, filed Jun. 15, 2006, the entire contents of which are incorporated herein by reference.

BACKGROUND OF THE INVENTION

1. Field of the Invention

The present invention relates to an endoscope provided with an observation optical system of an object contact type which brings a distal end portion of an objective optical system in contact with an object to observe the same.

2. Description of the Related Art

Jpn. Pat. Appln. KOKAI Publication No. 2005-640 (Patent Document 1) discloses an endoscope provided with an observation optical system of an object contact type and an ordinary observation optical system. The observation optical system of an object contact type brings a distal end portion of an objective optical system in contact with an object to observe the same. The ordinary observation optical system observes an object in a non-contact state of the objective optical system with the same. Here, the endoscope disclosed in Patent Document 1 includes a projecting portion projecting forward provided on a distal end face of an insertion portion of the endoscope. The observation optical system of an object contact type is disposed on an end face of the projecting portion. Further, an observation window of the ordinary observation optical system, windows of a plurality of illumination optical systems, a air-feeding/water-feeding nozzle, an distal end opening of a treatment tool insertion channel, and the like are disposed on an end face on a proximal end side of the projecting portion of the insertion portion. Illumination light is emitted ahead of the endoscope from an illumination window of the illumination optical system on the end face on the proximal end side of the projecting portion. The illumination light is used as illumination light for the ordinary observation optical system and is also used as illumination light for the observation optical system of an object contact type.

Jpn. Pat. Appln. KOKAI Publication No. 2002-238835 (Patent Document 2) shows an endoscope having a configuration where a projecting portion projecting forward is provided on a distal end face of an insertion portion of the endoscope. Here, an observation window of an observation optical system, an illumination window of an illumination optical system, a distal end opening of a first treatment tool insertion channel, and the like are disposed on an end face of the projecting portion at the distal end face of the insertion portion. Further, a distal end opening of a second treatment tool insertion channel is disposed on an end face on a root side of the projecting portion of the insertion portion.

BRIEF SUMMARY OF THE INVENTION

According to a first aspect of the present invention, an endoscope comprising a slender insertion portion having a distal end and a proximal end; and a distal end face disposed at the distal end of the insertion portion, where an observation portion for observing an area to be examined and an illumination portion emitting illumination light are disposed on the distal end face, wherein the observation portion has an observation window on which an observation image of the area to be examined is incident, and at least a distal end observation face of the observation window is disposed at a position projecting to a distal end side of the insertion portion beyond the distal end face.

In the endoscope with the abovementioned configuration, the projecting face provided at the distal end portion of the insertion portion for insertion into an area to be examined in the projecting manner is brought in contact with the area to be examined to press the illumination portion and the observation portion on the area to be examined, respectively during contact observation of the area to be examined. At this time, by disposing the distal end observation face of the observation window of the observation portion at a position projecting to the distal end side beyond the distal end face, it can be made easy to bring the entire distal end observation face of the observation window of the observation portion in contact with the area to be examined and illumination light from the illumination portion can be prevented from directly entering the observation window of the observation portion.

Preferably, the distal end face of the insertion portion is formed from an inclination face deviated from a direction orthogonal to an axial line direction of the insertion portion.

In the endoscope with the abovementioned configuration, by performing application to an endoscope of an inclination type where the distal end face of the insertion portion is formed in an inclined face to dispose the distal end observation face of the observation window of the observation portion at a position projecting to the distal end side beyond the end face of the inclined face, it can be made easy to bring the entire distal end observation face of the observation window of the observation portion in contact with the area to be examined and illumination light from the illumination portion can be prevented from directly entering the observation window of the observation portion.

Preferably, the distal end face includes at least a first face and a second face disposed at a portion projecting to a distal end side of the insertion portion beyond the first face, the observation portion and the illumination portion are disposed on the second face, and at least the distal end observation face of the observation portion is disposed so as to project to the distal end side beyond the second face.

In the endoscope with the abovementioned configuration, by disposing the distal end observation face of the observation portion of the second face disposed at a position projecting to the distal end side beyond the first face of the distal end face at a position projecting to the distal end side beyond the second face, it can be made easy to bring the entire distal end observation face of the observation window of the observation portion in contact with the area to be examined and illumination light from the illumination portion can be prevented from directly entering the observation window of the observation portion.

Preferably, the observation portion includes a first observation portion observing the area to be examined in a non-contact state therewith and a second observation portion observing the area to be examined in a contact state therewith, and at least the second observation portion is disposed on the second face.

In the endoscope with the abovementioned configuration, observation is performed by the first observation portion in a non-contacting state with the area to be examined and the second observation portion is brought in contact with the area to be examined to perform cell observation of a body tissue in a contacting state. At this time, by disposing the distal end observation face of the second observation portion of the second face disposed at a position projecting to the distal end side beyond the first face of the distal end face at a position projecting to the distal end side beyond the second face, it can be made easy to bring the entire distal end observation face of the second observation portion in contact with the area to be examined and illumination light from the illumination portion can be prevented from directly entering the observation window of the second observation portion.

Preferably, the distal end face includes at least a first face and a second face disposed at a position projecting to the distal end side beyond the first face, the observing portion observing the area to be examined and the illumination portion emitting illumination light are disposed on the second face, and a distal end observation face of the observation portion and a distal end face of an illumination window of the illumination portion are disposed at a position projecting to the distal end side beyond the second face.

In the endoscope with the abovementioned configuration, by disposing the distal end observation face of the observation portion of the second face and the distal end face of the illumination window of the illumination portion disposed at a position projecting to the distal end side beyond the first face of the distal end face at positions projecting to the distal end side beyond the second face, it can be made easy to bring the entire distal end observation face of the observation window of the observation portion in contact with the area to be examined and illumination light from the illumination portion can be prevented from directly entering the observation window of the observation portion.

Preferably, the distal end observation face of the observation portion is set to be smaller in projection amount from the second face than the distal end face of the illumination window of the illumination portion.

In the endoscope with the abovementioned configuration, by performing setting such that a projection amount of the distal end observation face of the observation portion from the second face is smaller than a projection amount of the distal end face of the illumination window of the illumination portion therefrom, illumination light from the illumination portion can be prevented from directly entering the observation window of the observation portion.

Preferably, the distal end observation face of the observation portion is set to be larger in projection amount from the second face than the distal end face of the illumination window of the illumination portion, and the observation portion includes, around the observation window, light-shielding means for preventing illumination light from the illumination portion from directly entering the distal end observation face.

In the endoscope with the abovementioned configuration, by disposing the distal end observation face of the observation portion and the distal end face of the illumination window of the illumination portion at the second face of the distal end face at positions projecting to the distal end side beyond the second face, it is made easy to bring the distal end observation face of the observation portion and the entire distal end face of the illumination window of the illumination portion in contact with the area to be examined, and when illumination light emitted from the distal end face of the illumination window of the illumination portion advances toward the distal end observation face of the observation portion, illumination light from the illumination portion is prevented from directly entering the distal end observation face by the light-shielding means around the observation window.

Preferably, the second observation portion has an observation optical system with a magnification higher than that of the first observation portion.

In the endoscope with the abovementioned configuration, observation is performed in a non-contacting state with the area to be examined by the first observation portion and the observation optical system with a high magnification of the second observation portion is brought in contact with the area to be examined to perform cell observation of body tissue in the contacting state. At this time, by disposing the observation optical system with high magnification of the second observation portion on the second face disposed at a position projecting to the distal end side beyond the first face of the distal end face at a position projecting to the distal end side beyond the second face, it can be made easy to bring the entire distal end observation face of the observation optical system with a high magnification of the second observation portion in contact with the area to be examined and illumination light from the illumination portion can be prevented from directly entering the observation window of the second observation portion.

BRIEF DESCRIPTION OF THE SEVERAL VIEWS OF THE DRAWING

FIG. 3 is a vertical sectional view showing an internal structure of an observation optical system of a contact and separation-combined type of an observation portion of the endoscope according to the first embodiment;

FIG. 10 is a vertical sectional view of a main part showing an internal structure of a distal end portion of an endoscope of a direct view type according to a fifth embodiment of the present invention;

DETAILED DESCRIPTION OF THE INVENTION

Figure 1:
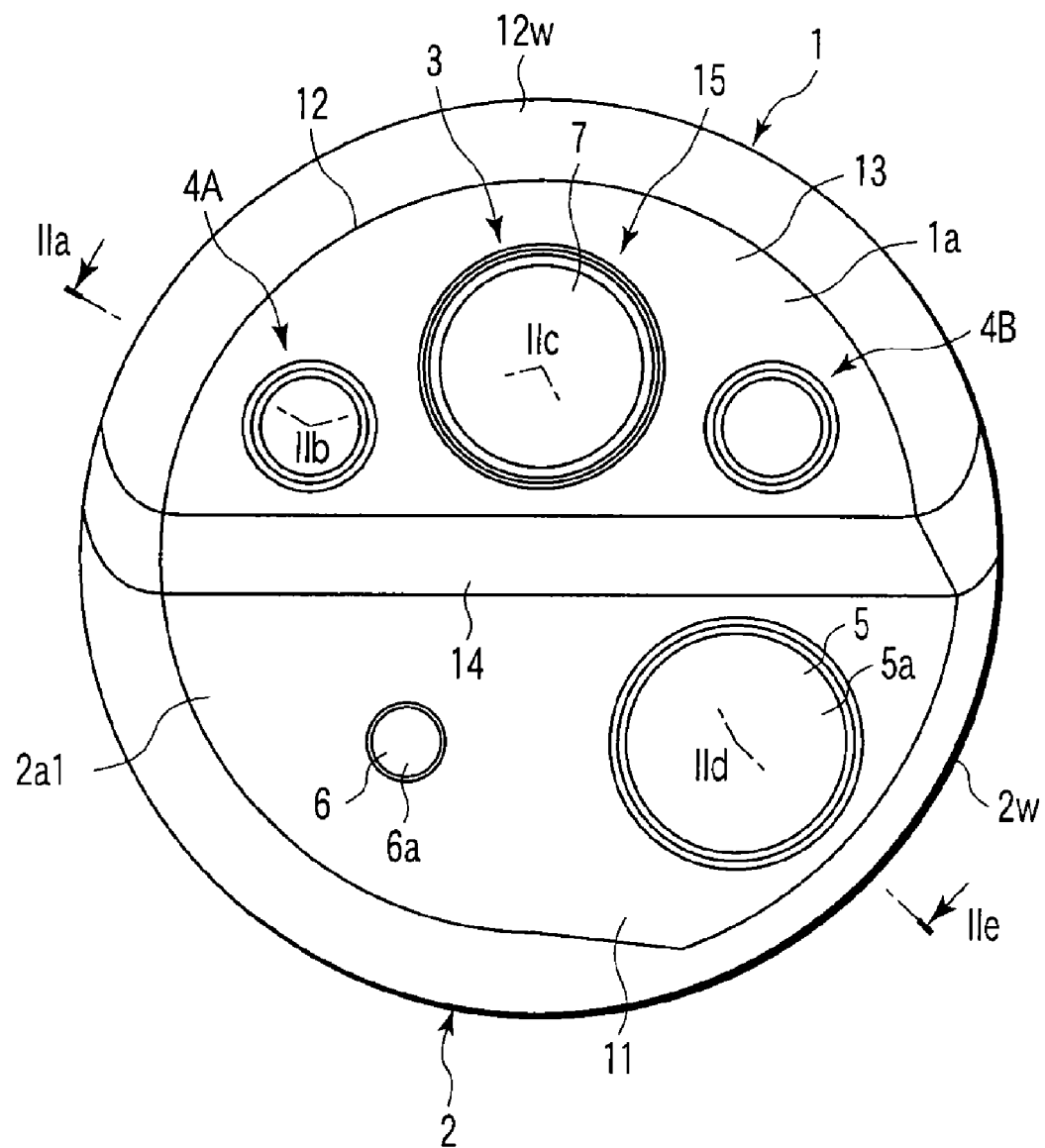
FIG. 1 is a front view of an end face of a distal end portion of an insertion portion of an endoscope showing a first embodiment of the present invention.

A first embodiment of the present invention will be explained below with reference to FIG. 1 to FIGS. 5A and 5B. FIG. 1 shows an end face 2a1 of an endoscope of a direct view type performing observation in a forward front face direction. In the endoscope of a direct view type, the end face 2a1 at a distal end portion 2 of an insertion portion 1 of the endoscope is disposed in a direction orthogonal to an axial direction of the insertion portion 1. An observation portion 3, two (first and second) illumination portions 4A and 4B, and a distal end opening 5a of a treatment tool insertion channel (also called "forceps channel") 5, and an opening 6a of a forward water-feeding conduit (forward water-feeding channel) 6 are disposed on the end face 2a1 of the distal end portion 2. The observation portion 3 observes an area to be examined. The first and second illumination portions 4A and 4B emit illumination lights. The treatment tool insertion channel 5 and the forward water-feeding conduit 6 are provided inside the insertion portion 1 to extend along an axial direction of the insertion portion 1, respectively.

An observation window 7 of an observation optical system (imaging unit) 15 (see FIG. 2) of a contact and separation-combined type described later is provided on the observation portion 3. The observation window 7 doubles as a first observation portion for performing observation in a non-contact state with an area to be examined and a second observation portion for performing observation in a contact state with the area to be examined.

Figure 2:
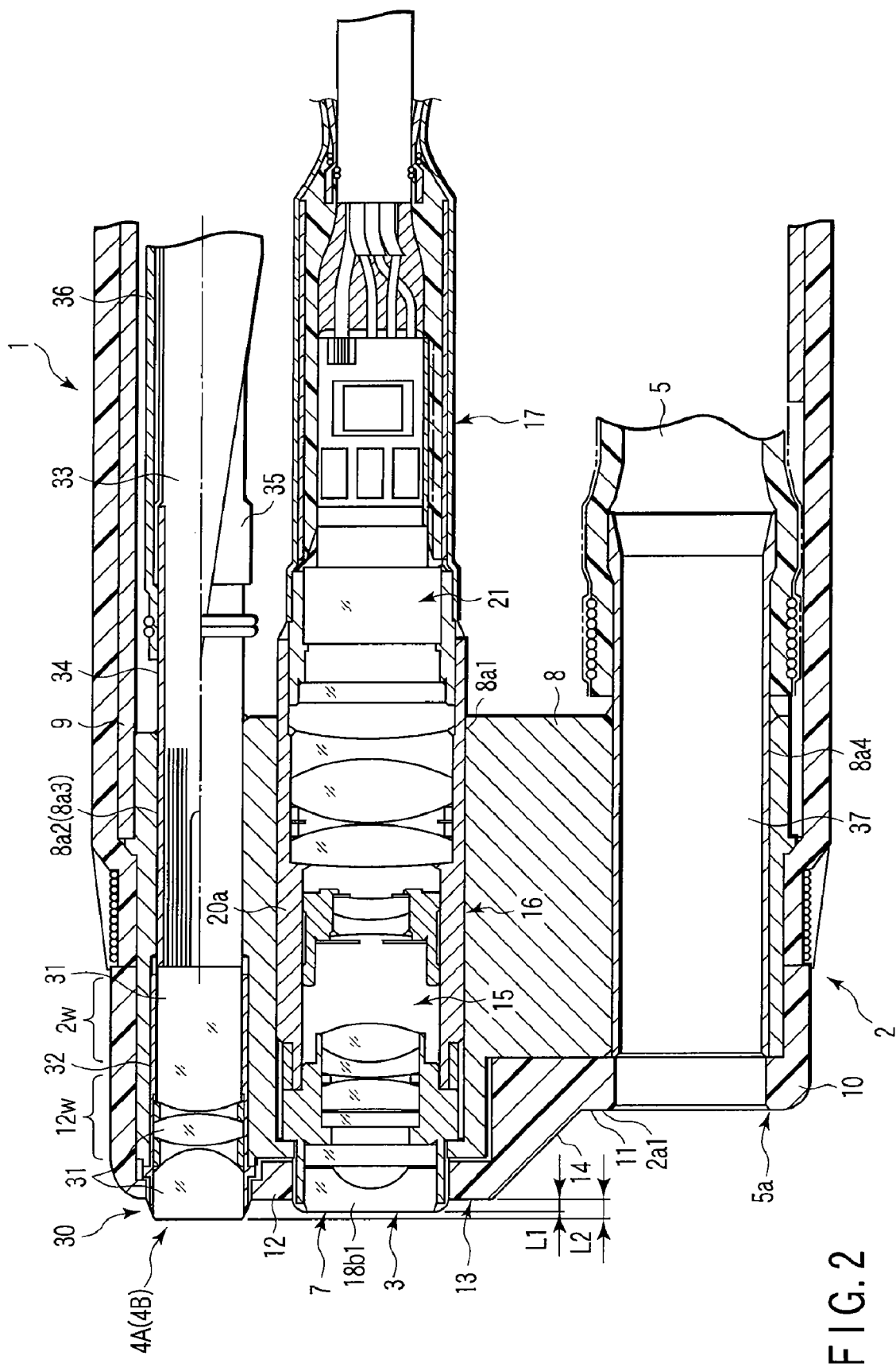
FIG. 2 is a sectional view of the endoscope, taken along lines IIa-IIb-IIc-IId-IIe in FIG. 1.

FIG. 2 shows an internal structure of a distal end portion of the insertion portion 1 of the endoscope according to the present embodiment. As shown in FIG. 2, a cylindrical member (distal end hard member) 8 made from hard metal and an annular reinforcing ring 9 are disposed within a distal end portion 2 of the insertion portion 1. The reinforcing ring 9 is fitted on an outer peripheral portion of the cylindrical member 8 at a proximal end side thereof. A plurality of, five (first to fifth) in the present embodiment, hole portions 8a1 to 8a5 (the fifth hole portion 8a5 is not illustrated) parallel to an axial direction of the insertion portion 1 are formed in the cylindrical member 8. A proximal end portion of the reinforcing ring 9 is coupled to a bending piece at a most forward end of a bending portion (not shown).

A distal end cover 10 is attached to a distal end face of the cylindrical member 8 and a distal end side outer peripheral portion of the cylindrical member 8 in an outer fitting manner. As shown in FIG. 2, a flat face-like base face (first face) 11 and a projecting portion 12 are formed on the distal end cover 10 disposed at the distal end portion 2 of the insertion portion 1. The base face 11 is provided so as to extend in a direction orthogonal to the axial direction of the insertion portion 1. The projecting portion 12 projects forward from the base face 11. A projecting face (second face) 13 is formed on a distal end face of the projecting portion 12. The projecting face 13 is positioned in parallel with the base face 11. Incidentally, an inclined face 14 with an inclination angle of, for example, about 45° is formed on a wall portion between the base face 11 and the projecting portion 12.

In the present embodiment, the projecting face 13 of the projecting portion 12 is formed so as to occupy an area of about ½ of an area of the entire circular front face of the distal end cover 10. That is, as shown in FIG. 1, the projecting face 13 is formed at an upper half portion of the entire circular front face of the distal end cover 10.

Further, in the present embodiment, as shown in FIG. 2, a continuous peripheral wall face obtained by continuously forming an outer peripheral wall face 12w of the projecting portion 12 and an outer peripheral wall face 2w of the distal end portion 2 on the same curved face is formed on an outer peripheral face of the distal end cover 10 of the insertion portion 1. As shown in FIG. 1, the continuous peripheral wall face is formed so as to occupy an area corresponding to about a half circumference of the entire circular outer peripheral faces of the distal end cover 10.

An observation window 7 of an observation optical system of a contact and separation-combined type and first and second illumination portions 4A and 4B are disposed on the projecting face 13 of the projecting portion 12. Here, the observation window 7 is disposed at an approximately central position of the projecting face 13. The first and second illumination portions 4A and 4B are arranged on both sides of the observation window 7. Further, the distal end opening 5a of the treatment tool insertion channel 5 and the opening 6a of the forward water-feeding conduit 6 are disposed on the base face 11.

Three (first to third) hole portions 8a1 to 8a3 of the cylindrical member 8 of the distal end portion 2 are disposed at sites corresponding to the observation portion 3 and the first and second illumination portions 4A and 4B of the projecting portion 12. Respective constituent elements of the observation portion 3, respective constituent elements of the first illumination portion 4A, and the respective constituent elements of the second illumination portion 4B are assembled in the first hole portion 8a1, the second hole portion 8a2, and the third hole portions 8a3 of the cylindrical member 8.

Further, the remaining two (fourth and fifth) hole portions 8a4 and 8a5 of the cylindrical member 8 are arranged at sites corresponding to the distal end opening 5a of the treatment tool insertion channel 5 of the base face 11 and the opening 6a of the forward water-feeding conduit 6, respectively. Constituent elements of the treatment tool insertion channel 5 are coupled to the fourth hole portion 8a4 of the cylindrical member 8. Similarly, constituent elements of the forward water-feeding conduit 6 are coupled to the fifth hole portion 8a5 (not shown) of the cylindrical member 8.

An observation optical system 15 of a contact and separation-combined type is provided in the observation portion 3. FIG. 3 shows an internal structure of the observation optical system 15 of a contact and separation-combined type. The observation optical system 15 of the contact and separation-combined type includes a zoom lens unit 16 provided with a zoom optical system where an observation magnification can be changed from Tele (expansion) position to Wide (wide-angle) position and an electronic parts unit 17.

The zoom lens unit 16 further includes four (first to fourth) unit configuration bodies 18 to 21. The first unit configuration body 18 includes a first lens frame 18a and a first lens group 18b configuring an objective lens. As shown in FIG. 2, the first lens group 18b includes six (first to sixth) lenses 18b1 to 18b6. Here, the first lens 18b1 which is an observation lens forming the observation window 7 is disposed at the foremost end portion of the first lens frame 18a. The first lens 18b1 is bonded and fixed to the first lens frame 18a by, for example, black adhesive 22 in a state that a distal end portion (distal end observation face) of the first lens 18b1 projects forward beyond the distal end portion of the first lens frame 18a. Thereby, a portion of the first lens 18b1 on a distal end outer peripheral face thereof which projects forward beyond the distal end portion of the first lens frame 18a is held in a state that it has been covered with the black adhesive 22.

The second unit configuration body 19 is a moving optical unit for zooming which can advance and retreat in an imaging optical axis direction. The second unit configuration body 19 includes a second lens frame (sliding lens frame) 19a and a second lens group (zoom lens) 19b. The second lens group 19b has two (first and second) lenses 19b1 and 19b2.

The third unit configuration body 20 includes a third lens frame 20a and a third lens group 20b. A guide space 20c holding the second unit configuration body 19 so as to be capable of advancing and retreating in the imaging optical axis direction is provided within the third lens frame 20a. The third lens group 20b is disposed behind the guide space 20c. The third lens group 20b includes three (first to third) lenses 20b1 to 20b3.

The fourth unit configuration body 21 includes a fourth lens frame 21a and fourth lens group 21b. The fourth lens group 21b includes two (first and second) lenses 21b1 and 21b2.

A distal end portion of an operation wire (not shown) for operating the second unit configuration body 19 so as to advance and retreat in the imaging optical axis direction is fixed to the second lens frame 19a of the second unit configuration body 19. The operation wire is driven so as to advance and retreat in the imaging optical axis direction according to operation to an operation lever for zooming (not shown) provided on an operation portion of the endoscope in the imaging optical axis direction performed by a user. At this time, the second unit configuration body 19 which is a zoom optical system is moved forward (in a Wide (wide angle) position direction) according to operation where the operation wire is pushed in the distal end direction. Further, the second unit configuration body 19 which is the zoom optical system is moved toward the near side (Tele (expansion) position direction) according to operation where the operation wire is pulled in the near side. Here, a state that the second unit configuration body 19 has been moved to a position other than the rearmost end position of the guide space 20c of the third unit configuration body 20 is set in a range of a first observation position (ordinary observation) for observing an area to be examined in a non-contacting state therewith. A state that the second unit configuration body 19 has been moved to the rearmost end position of the guide space 20c is set in a second observation position (an object contact observation with monitor observation magnification of about 200 times to 1000 times) for observing an area to be examined in a contacting state therewith. Thereby, switching between the first observation position for observing an area to be examined in a non-contacting state therewith and the second observation position for observing an area to be examined in a contacting state therewith can be performed according to operation of the operation lever for zooming (not shown).

A brightness aperture 23 is provided at the second lens frame 19a in the sliding second unit configuration body 19 for zooming. The brightness aperture 23 is disposed on a front face side of the first lens 19b1 held by the second lens frame 19a. An opening 23b through which light can pass is provided at a central portion of a light-shielding sheet 23a in the brightness aperture 23.

A plurality of, two in the present embodiment, spacer rings 24 are interposed between the first lens 20b1 and the second lens 20b2 in the third unit configuration body 20 as positioning members for determining a distance between lenses. A flare aperture 25 for preventing optical flare is interposed between the two spacer rings 24.

Further, an electric parts unit 17 is provided at a rear end portion of the fourth unit configuration body 21 in continuous manner. The electric parts unit 17 includes an imaging device 26 such as a CCD (Charge Coupled Device) or a CMOS (Complementary Metal-Oxide Semiconductor) and a circuit board 27. Further, a cover glass 28 is provided on the side of a light receiving face of the front face of the imaging device 26.

The cover glass 28 of the electric parts unit 17 is fixed in a state that it is provided in parallel with the second lens 21b2 of the fourth unit configuration body 21. Thereby, the observation optical system 15 of a contact and separation-combined type where the zoom lens unit 16 and the electric parts unit 17 have been unitized is formed.

The circuit board 27 has electric parts and a wiring pattern, and it is connected with distal end portions of a plurality of signal lines of a signal cable 29 by means of soldering or the like. Further, respective cuter peripheral portions of the cover glass 28, the imaging device 26, the circuit board 27 and a distal end portion of the signal cable 29 are integrally covered with an insulating sealing resin or the like.

An optical image focused on the imaging device 26 from the zoom lens unit 16 is photoelectically converted to electric image signal by the imaging device 26 and the image signal is output to the circuit board 27. Further, electric signal of an optical image output from the circuit board 27 is transmitted to an electric apparatus (not shown) subsequent via the signal cable 29.

As shown in FIG. 2, the observation optical system 15 of a contact and separation-combined type is bonded, assembled and fixed to the cylindrical member 8 in a state that it has been inserted into the first hole portion 8a1 of the cylindrical member 8. Here, fixation is made in a state that a front end portion of the first lens 18b1 of the first unit configuration body 18 has projected forward from a position of the projecting face 13 of the projecting portion 12 by a proper length L1, for example, about 0.05 mm.

The first and second illumination portions 4A and 4B have approximately the same configuration. Therefore, only the configuration of the first illumination portion 4A is here explained and explanation of the second illumination portion 4B is omitted. An illumination lens unit 30 is provided in the first illumination portion 4A. The illumination lens unit 30 has a plurality of illumination lenses 31 and a holding frame 32 for holding the illumination lenses 31.

Further, the illumination lenses 31 of the illumination lens unit 30 are inserted and fitted into a front end portion of the second hole portion 8a2 of the cylindrical member 8 of the distal end portion 2. Fixation is made in a state that a front end portion of the illumination lens 31 of the first illumination portion 4A has been projected forward beyond a position of the projecting face 13 of the projecting portion 12. Here, a projecting length L2 of the front end portion of the illumination lens 31 from the projecting face 13 of the projecting portion 12 is set to, for example, about 0.1 mm. The front end portion of the illumination lens 31 of the first illumination portion 4A is projected forward beyond the front end portion position of the first lens 18b1 of the first unit configuration body 18 of the observation optical system 15 and a relationship of $L2>L1>0$ is satisfied.

A distal end portion of a light guide 33 transmitting illumination light is inserted and fitted into a rear end portion of the second hole portion 8a2. The light guide 33 has a distal end portion covered with a cylindrical member 34 and is covered with an outer skin 35 bundling a plurality of fiber filaments and a protective tube 36 which is a goa material.

The light guide 33 sequentially penetrates insides of the insertion portion 1, an operation portion of the endoscope, and a universal cable (not shown) to extend into a connector. A proximal end portion side of the light guide 33 is connected to a light guide connector (not shown) projecting from the connector. The light guide connector is connected to a light source apparatus (not shown) in an attachable and detachable manner.

In the present embodiment, the light guide 33 is branched, for example, within the operation portion of the endoscope so that it is inserted into the insertion portion 1 in a state that it has been divided to two pieces. Distal end portions of respective light guides 33 divided in two pieces are disposed so as to face two illumination windows provided at the distal end cover 10, namely, vicinities of back faces of respective illumination lenses 31 of the first illumination portion 4A and the second illumination portion 4B, and they are fixed to rear end portions of the second hole portion 8a2 and the third hole portion 8a3 of the cylindrical member 8, for example, by screw cramp.

Irradiation of illumination light from the light source apparatus is performed to a proximal end portion of the light guide 33 and illumination light guided through the light guide 33 is emitted ahead of the endoscope via respective illumination lenses 31 of the first illumination portion 4A and the second illumination portion 4B.

A distal end portion of a communicating tube 37 communicating with the treatment tool insertion channel 5 is inserted and fitted into the fourth hole portion 8a4 formed in the cylindrical member 8 of the distal end portion 2 from the proximal end portion side of the fourth hole portion 8a4. A proximal end portion of the communicating tube 37 projects behind the cylindrical member 8, and the distal end portion of the treatment tool insertion channel 5 is coupled to the proximal end portion of the communicating tube 37. A distal end of the treatment tool insertion channel 5 communicates with the distal end opening 5a of the distal end cover 10 via the communicating tube 37.

The treatment tool insertion channel 5 is branched near a proximal end of the insertion portion 1 and one of the branched portions is inserted up to a treatment tool inlet (not shown) disposed in the operation portion of the endoscope. The other of the branched portions communicates with a suction channel through the insertion portion 1 and a universal cable (not shown) and a proximal end thereof is connected to suction means (not shown) via a connector.

A distal end portion of an approximately cylindrical tubular member is inserted and fitted into the fifth hole portion 8a5 formed in the cylindrical member 8 of the distal end portion 2 from rear end portion side of the fifth hole portion 8a5. A proximal end portion of the tubular member projects behind the cylindrical member 8 and a distal end portion of the forward water-feeding conduit 6 is coupled to a proximal end portion of the tubular member. Incidentally, the distal end portion of the forward water-feeding conduit 6 covers the proximal end portion of the tubular member and connection and fixation of the distal end portion is performed by bobbin winding.

The forward water-feeding conduit 6 reaches the connector through the insertion portion 1, the operation portion of the endoscope, and the universal cable, and it is connected to a forward water-feeding apparatus (not shown). A forward water-feeding button (not shown) is provided in a halfway portion of the forward water-feeding conduit 6 in the operation portion of the endoscope.

When the forward water-feeding button is operated, liquid such as sterile water is blown from the opening 6a of the distal end cover 10 of the insertion portion 1 in an insertion direction to a body cavity. Thereby, body fluid or the like adhering to a site to be examined in the body cavity can be cleaned.

Next, an operation of the endoscope with the abovementioned configuration will be explained. At a time of use of the endoscope according to the present embodiment, after setting of an endoscope system is terminated, a work for inserting the endoscope into a body of a patient is started. A user sets the second unit configuration body 19 which is the zoom optical system of the observation optical system 15 of a contact and separation-combined type of the observation portion 3 in the range of the first observation position where an area to be examined is observed in a non-contacting state therewith in advance during an insertion work of the endoscope. The insertion portion 1 of the endoscope is inserted into a body cavity so that setting is performed such that an affected area or the like can be observed in the ordinary observation state.

Illumination light of, for example, RGB from the light source apparatus is supplied to the light guide 33 in a frame sequential manner. In synchronism therewith, a drive circuit outputs a CCD drive signal to illuminate the affected area or the like within the body cavity of the patient via the first illumination portion 4A and the second illumination portion 4B.

A subject of the affected area or the like illuminated is focused on a light receiving face of the imaging device 26 through the zoom lens unit 16 of the observation optical system 15 at the ordinary observation position to be photoelectrically converted. When the imaging device 26 is applied with a drive signal, it outputs a photoelectrically converted signal. The signal is input into an external signal processing circuit (not shown) via a signal cable 29. The signal input into the signal processing circuit is temporarily stored in a memory for R, G, and B after A/D-converted.

Thereafter, signals stored in the memory for R, G, and B are simultaneously read to form R, G, and B signals synchronized, and the R, G, and B signals are D/A-converted to analog R, G, and B signals so that color display is performed on a monitor. Thereby, the ordinary observation for observing an observation object separated from the first lens 18b1 of the zoom lens unit 16 of the observation optical system 15 in a wide range is performed using the zoom lens unit 16 of the observation optical system 15 at the ordinary observation position.

When the site to be examined within the body cavity is contaminated due to adhesion of body fluid or the like thereto during ordinary observation, the forward water-feeding button is operated. Body liquid such as sterile water is blown from the opening 6a of the distal end cover 10 of the insertion portion 1 in the insertion direction to the body cavity at an operation time of the forward water-feeding button. Thereby, the body liquid or the like adhering to the site to be examined within the body cavity can be cleaned.

The observation performed by the zoom lens unit 16 of the observation optical system 15 at the ordinary observation position is continued until the distal end portion of the endoscope inserted into the body of the patient reaches a target observation object site. The operation lever for zooming is operated by a user in a state that the distal end portion of the endoscope has approached the target observation object site, so that switching to a state that the second unit configuration body 19 of the zoom lens unit 16 of the observation optical system 15 has moved to the rearmost end position of the guide space 20c is performed and switching to the second observation position (object contact observation with a high magnification) observing an area to be examined in a contacting state therewith is performed.

Figure 5A:
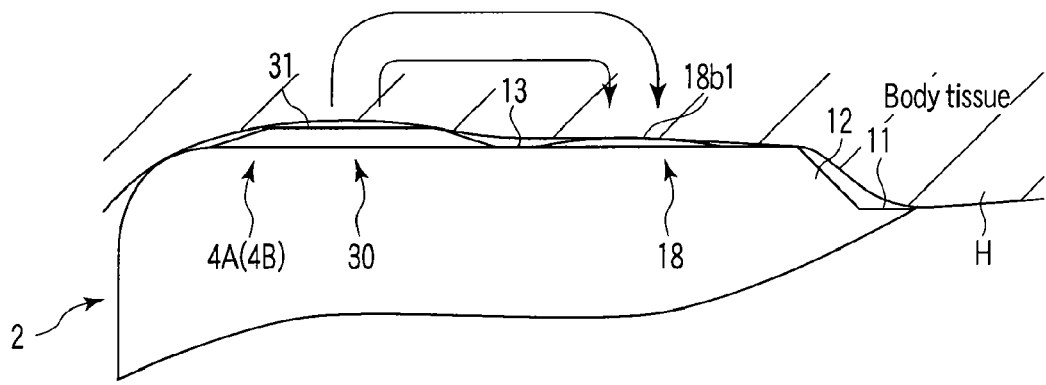
FIG. 5A is a vertical sectional view of a main part showing an observation state performed by an observation optical system of an object contact type where a lens of the endoscope according to the first embodiment has projected.

As shown in FIG. 5A, the projecting face 13 of the projecting portion 12 of the distal end portion 2 of the insertion portion 1 is pressed on a surface of a body tissue H which is an object in a state that switching to the observation mode with a high magnification has been performed in this manner. At this time, the projecting face 13 of the projecting portion 12 of the distal end cover 10 is mainly pressed on the surface of the body tissue H, but non-projecting faces such the base face 11 other than the projecting face 13 are held in a non-contact state with the surface of the body tissue H. Therefore, the first lens 18b1, and the illumination lenses 31 of the first and second illumination portions 4A and 4B at the distal end of the observation optical system 15 disposed on the projecting face 13 of the projecting portion 12 are brought in pressure contact with the surface of the body tissue H such as a cell tissue of an observation object. Incidentally, when the surface of the body tissue H such as the cell tissue of the observation object is observed with a high magnification in a magnifying manner, for example, pigment is sprayed on an interesting site in advance and the interesting site is dyed so that a contour of the cell can be observed sharply.

In this state, such an object contact observation with a high magnification is performed that the first lens 18b1 and the illumination lenses 31 of the first and second illumination portions 4A and 4B at the distal end of the observation optical system 15 on the projecting face 13 of the projecting portion 12 are brought in contact with the surface of the body tissue H and a cell tissue of the observation object or the like is observed with a high magnification.

The body tissue H such as a cell tissue is irradiated with illumination light through the illumination lenses 31 of the first and second illumination portions 4A and 4B during cell observation of the body tissue H performed by the observation optical system 15 of an object contact type. At this time, a portion of the illumination light applied for irradiation to the body tissue H such as a cell tissue reaches inside of the body tissue H such as a cell tissue, as shown by arrow in FIG. 5A, so that it is also diffused around abutting faces of the illumination lenses 31 of the first and second illumination portions 4A and 4B. Therefore, a surrounding portion of the body tissue H such as a cell tissue ahead of the first lens 18b1 of the observation optical system 15 is also irradiated with illumination light. Thereby, a portion which is observed by the first lens 18b1 of the observation optical system 15 which has been pressed on the surface of the body tissue H such as a cell tissue is also irradiated with illumination light so that light of the body tissue H such a cell tissue is focused on the light receiving face of the imaging device 26 through the zoom lens unit 16 of the observation optical system 15 to be photoelectrically converted.

The imaging device 26 outputs photoelectrically-converted signals. In this case, the signals are amplified within the imaging device 26 to be output from the imaging device 26. The signals are input into the external signal processing circuit via the signal cable 29.

After the signals input into the signal processing circuit are A/D-converted therein, they are simultaneously stored in the memory for R, G, and B, for example. Thereafter, the signals stored in the memory for R, G, and B are simultaneously read to form synchronized R, G, and B signals, they are D/A-converted to analog R, G, and B signals so that display is performed on the monitor. Thereby, observation of the body tissue H such as a cell tissue ahead of the first lens 18b1 of the observation optical system 15 is performed in the observation mode with a high magnification using the observation optical system 15 of an object contact type.

Therefore, the following effects can be achieved in the endoscope with the abovementioned configuration. That is, according to the present embodiment, the first lens 18b1 which is the observation lens of the observation optical system 15 of a contact and separation-combined type and the first and second illumination portions 4A and 4B are disposed on the projecting face 13 of the projecting portion 12 of the distal end portion 2 of the insertion portion 1, and the distal end observation face of the first lens 18b1 of the observation window 7 of the observation optical system of a contact and separation-combined type of the observation portion 3 and the first and second illumination portions 4A and 4B are disposed at a position projecting to the distal end side beyond the projecting face 13 of the projecting portion 12. By disposing the distal end observation face of the first lens 18b1 of the observation optical system 15 and the first and second illumination portions 4A and 4B at the position projecting to the distal end side beyond the projecting face 13 of the distal end portion 2 in this manner, when the projecting face 13 of the distal end portion 2 of the insertion portion 1 is pressed on an area to be examined at a contact observation time of the area to be examined, it can be made easy to bring all of the distal end observation face of the first lens 18b1 which is the observation lens of the observation optical system 15 and the first and second illumination portions 4A and 4B in contact with the body tissue H of the area to be examined.

Figure 5B:
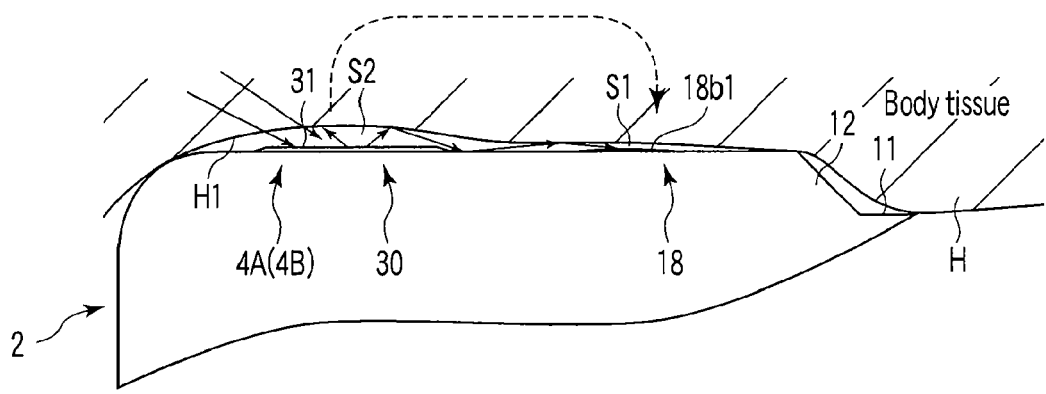
FIG. 5B is a vertical sectional view of a main part showing an observation state performed by the observation optical system of the object contact type where the lens has not been projected.

Here, as shown in FIG. 5B, when the first lens 18b1 of the observation optical system 15 and the first and second illumination portions 4A and 4B disposed on the projecting face 13 of the projecting portion 12 of the distal end portion 2 of the insertion portion 1 do not project from the projecting face 13 of the projecting portion 12, such a case may occur that, even if the projecting portion 12 of the distal end portion 2 of the insertion portion 1 is pressed on the a surface H1 of the body tissue H, the first lens 18b1 of the observation optical system 15 and the first and second illumination portions 4A and 4B on the projecting face 13 of the projecting portion 12 of the distal end portion 2 of the insertion portion 1 cannot be brought in contact with the surface H1 of the body tissue H accurately. For example, when wave, undulation, or the like is formed on the surface H1 of the body tissue H, there is a possibility that, even if the projecting portion 12 of the distal end portion 2 of the insertion portion 1 is pressed on the surface H1 of the body tissue H, a gap S1 is formed between the first lens 18b1 of the observation optical system 15 of the projecting face 13 of the projecting portion 12 of the distal end portion 2 of the insertion portion 1 and the surface H1 of the body tissue H so that gaps S2 are formed between the first and second illumination portions 4A and 4B and the surface H1 of the body tissue H. In such a case, there is such a possibility that scattering occurs in illumination light emitted from the first and second illumination portions 4A and 4B and a portion of the illumination light enters the first lens 18b1 of the observation optical system 15 directly so that adverse effect such flare occurs during cell observation from the observation window.

On the other hand, when the distal end observation face of the first lens 18b1 of the observation window 7 of the observation optical system of a contact and separation-combined type of the observation portion 3 and the first and second illumination portions 4A and 4B are disposed at the position projecting to the distal end side beyond the projecting face 13 of the projecting portion 12 like the present embodiment, it can be made easy to bring all of the distal end observation face of the first lens 18b1 which is the observation lens of the observation optical system 15 and the first and second illumination portions 4A and 4B in contact with the body tissue H of the area to be examined when the projecting face 13 of the distal end portion 2 of the insertion portion 1 is pressed on the area to be examined at a contact observation time of the area to be examined. Therefore, even if wave, undulation, or the like is formed on the surface H1 of the body tissue H, such an event can be prevented that, when the projecting portion 12 of the distal end portion 2 of the insertion portion 1 is pressed on the surface H1 of the body tissue H, the gap S1 is formed between the first lens 18b1 of the observation optical system 15 on the projecting face 13 of the projecting portion 12 of the distal end portion 2 of the insertion portion 1 and the surface H1 of the body tissue H or the gaps S2 are formed between the first and second illumination portions 4A and 4B and the surface H1 of the body tissue H. As a result, scattering can be prevented from occurring in illumination light emitted from the first and second illumination portions 4A and 4B so that adverse effect such as flare can be prevented from occurring due to direct incidence of a portion of illumination light into the first lens 18b1 of the observation optical system 15 during cell observation from the observation window.

Further, when the projecting portion 12 of the distal end portion 2 of the insertion portion 1 is pressed on the surface H1 of the body tissue H, if a gap S1 is formed between the first lens 18b1 of the observation optical system 15 and the surface H1 of the body tissue H, scattering occurs in illumination light emitted from the first and second illumination portions 4A and 4B, so that intensity of transmitted light which has passed through the surface H1 of the body tissue H becomes weak. Therefore, there is a possibility that it become difficult to obtain a sharp observation image such as cell observation of the body tissue H observed by the first lens 18b1 of the observation optical system 15 which has been caused to abut on the surface H1 of the body tissue H.

Figure 4A:
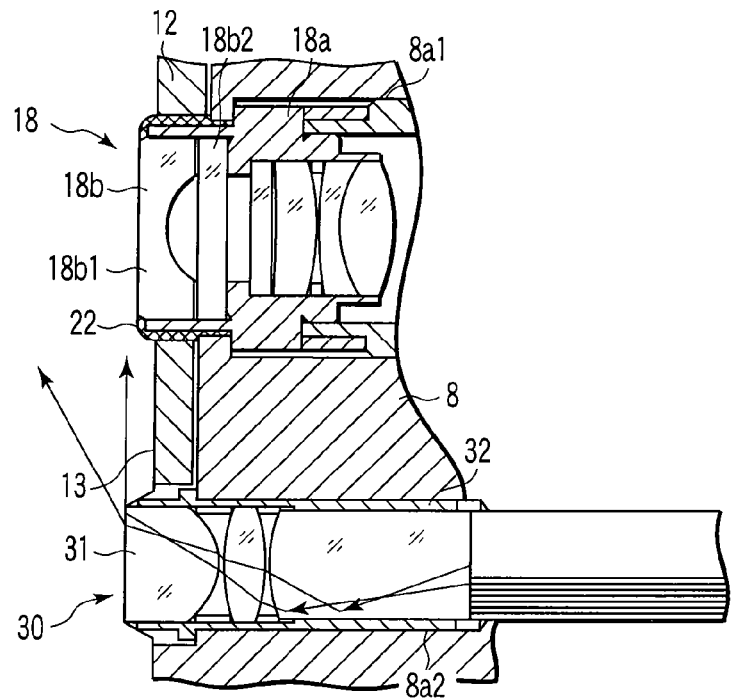
FIG. 4A is a vertical sectional view of a main part showing a state that a distal end face of an illumination window of an illumination portion of the endoscope according to the first embodiment projects forward beyond a distal end observation face of the observation portion.

Further, in the present embodiment, the relationship between the projecting length L1 of the front end portion of the first lens 18b1 of the first unit configuration body 18 and the projecting length L2 of the front end portion of the illumination lens 31 is set to satisfy the relationship of L2>L1>0, and the front end portion of the illumination lens 31 of the first illumination portion 4A projects forward beyond the front end portion position of the first lens 18b1 of the first unit configuration body 18 of the observation optical system 15. As shown in FIG. 4A, therefore, there is not a possibility that, even if illumination light is emitted from the front end portion of the illumination lens 31 of the first illumination portion 4A in a direction orthogonal to the axial direction, the illumination light enters the first lens 18b1 of the first unit configuration body 18 of the observation optical system 15 directly. Therefore, such an event can be prevented that a portion of illumination light directly enters the first lens 18b1 of the observation optical system 15 so that adverse effect such as flare occurs during cell observation from the observation window.

Figure 4B:
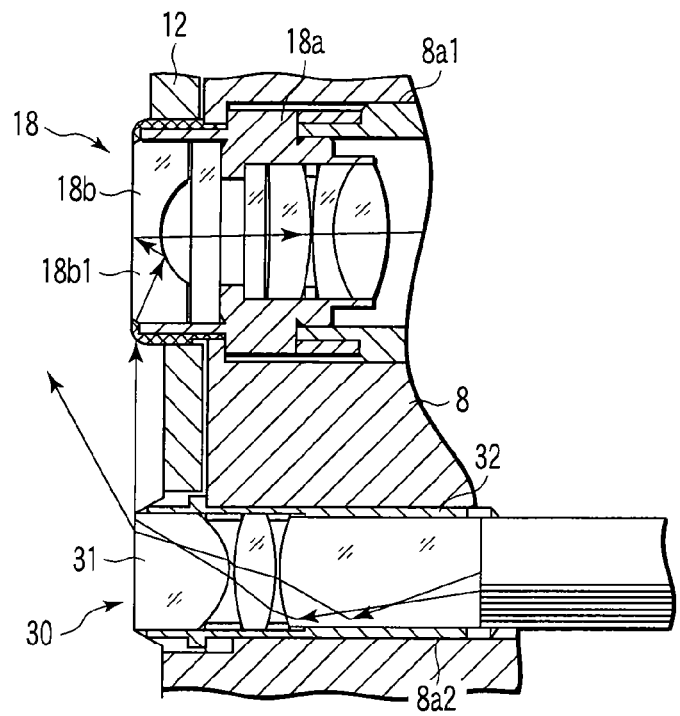
FIG. 4B is a vertical sectional view of a main part showing a state that the distal end observation face of the observation portion of the endoscope has been set to be flush with the distal end face of the illumination window of the illumination portion.

On the other hand, as shown in FIG. 4B, when the relationship between the projecting length L1 of the front end portion of the first lens 18b1 of the first unit configuration body 18 and the projecting length L2 of the front end portion of the illumination lens 31 is set to satisfy the relationship of L2=L1>0, there is a possibility that, when illumination light is emitted from the front end portion of the illumination lens 31 of the first illumination portion 4A in a direction orthogonal to the axial direction, the illumination light directly enters the first lens 18b1 of the first unit configuration body 18 of the observation optical system 15. Especially, when the first lens 18b1 is bonded and fixed to the first lens frame 18a by black adhesive 22 in a state that the distal end portion of the first lens 18b1 has projected forward beyond the distal end portion of the first lens frame 18a, there is a possibility that illumination light emitted in a direction orthogonal to the axial direction proceeds into a thin portion of the black adhesive 22 from the front end portion of the illumination lens 31 of the first illumination portion 4A. In this case, therefore, there is a possibility that a portion of the illumination light directly enters the first lens 18b1 of the observation optical system 15 so that adverse effect such as flare occurs during cell observation or ordinary observation (an area to be examined is observed in a non-contacting state therewith) from the observation window.

Further, in the present embodiment, as shown in FIG. 2, the continuous circumferential wall face obtained by continuously forming an outer circumferential wall face 12w of the projecting portion 12 and an outer circumferential wall face 2w of the distal end portion 2 on the same curved face is formed on an outer circumferential face of the distal end cover 10 of the insertion portion 1 so as to occupy a range of an approximately half circle of the entire cylindrical outer circumferential face of the distal end cover 10, as shown in FIG. 1. Therefore, a dead space formed around the outer circumferential wall face 2w of the distal end portion 2 can be reduced as compared with a case that the continuous circumferential wall face continuously formed on the same curved face as the outer circumferential wall face 2w of the distal end portion 2 is not formed on the outer circumferential face of the projecting portion 12 of the distal end cover 10. As a result, an outer diameter size of the entire distal end portion 2 of the insertion portion 1 can be reduced so that size reduction of the entire distal end portion 2 of the insertion portion 1 can be achieved.

In the present embodiment, since the observation optical system 15 of the imaging unit provided with the zoom optical system which can perform zooming action from the ordinary observation position to the expansion (Wide) observation position with a high magnification is used, an entire installation space for the imaging unit can be reduced as compared with a case that an imaging unit for ordinary observation and an imaging unit for expansion observation with a high magnification are provided separately from each other.

Figure 6:
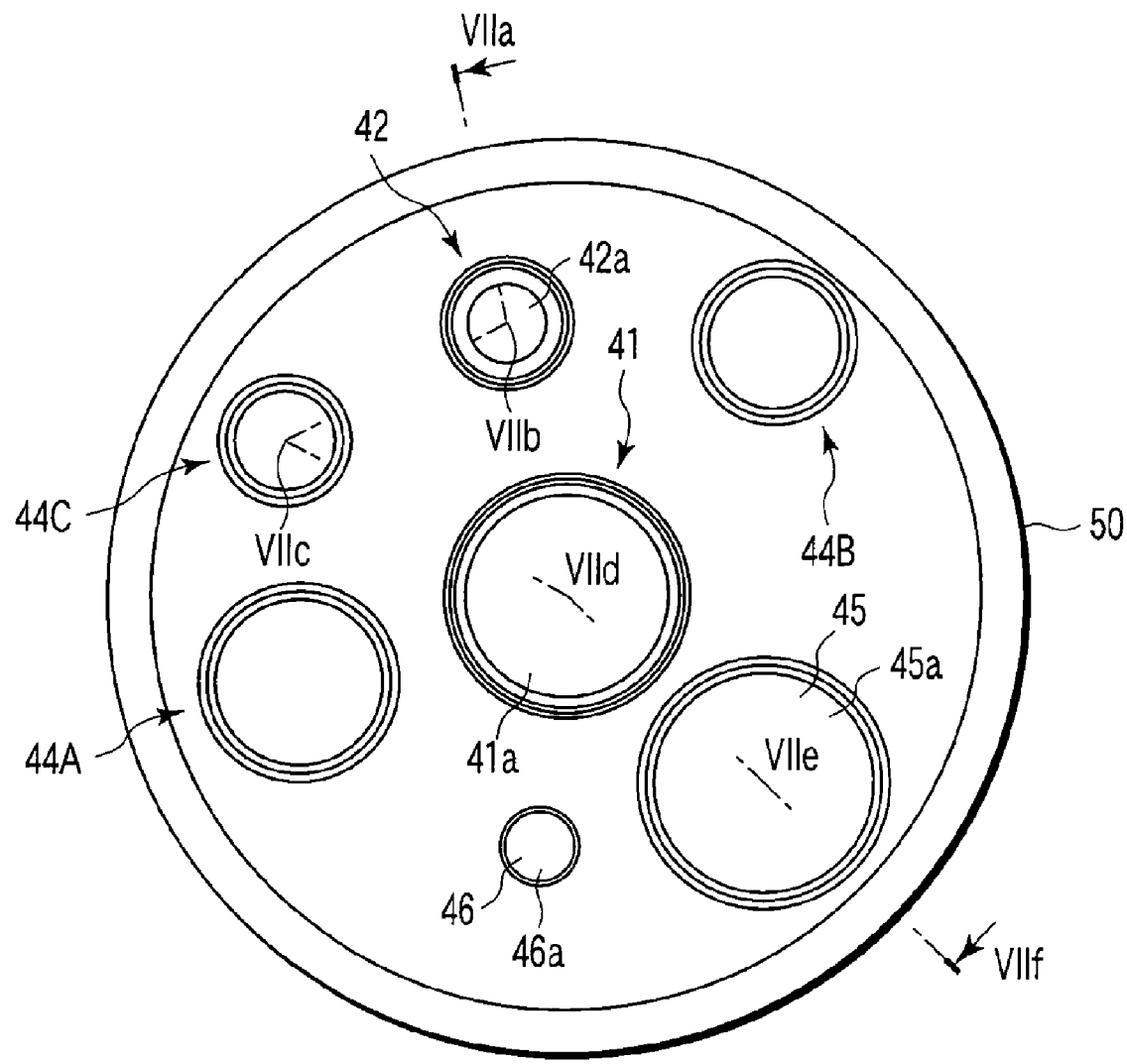
FIG. 6 is a front view showing a distal end portion of an endoscope of a direct view type according to a second embodiment of the present invention.
Figure 7:
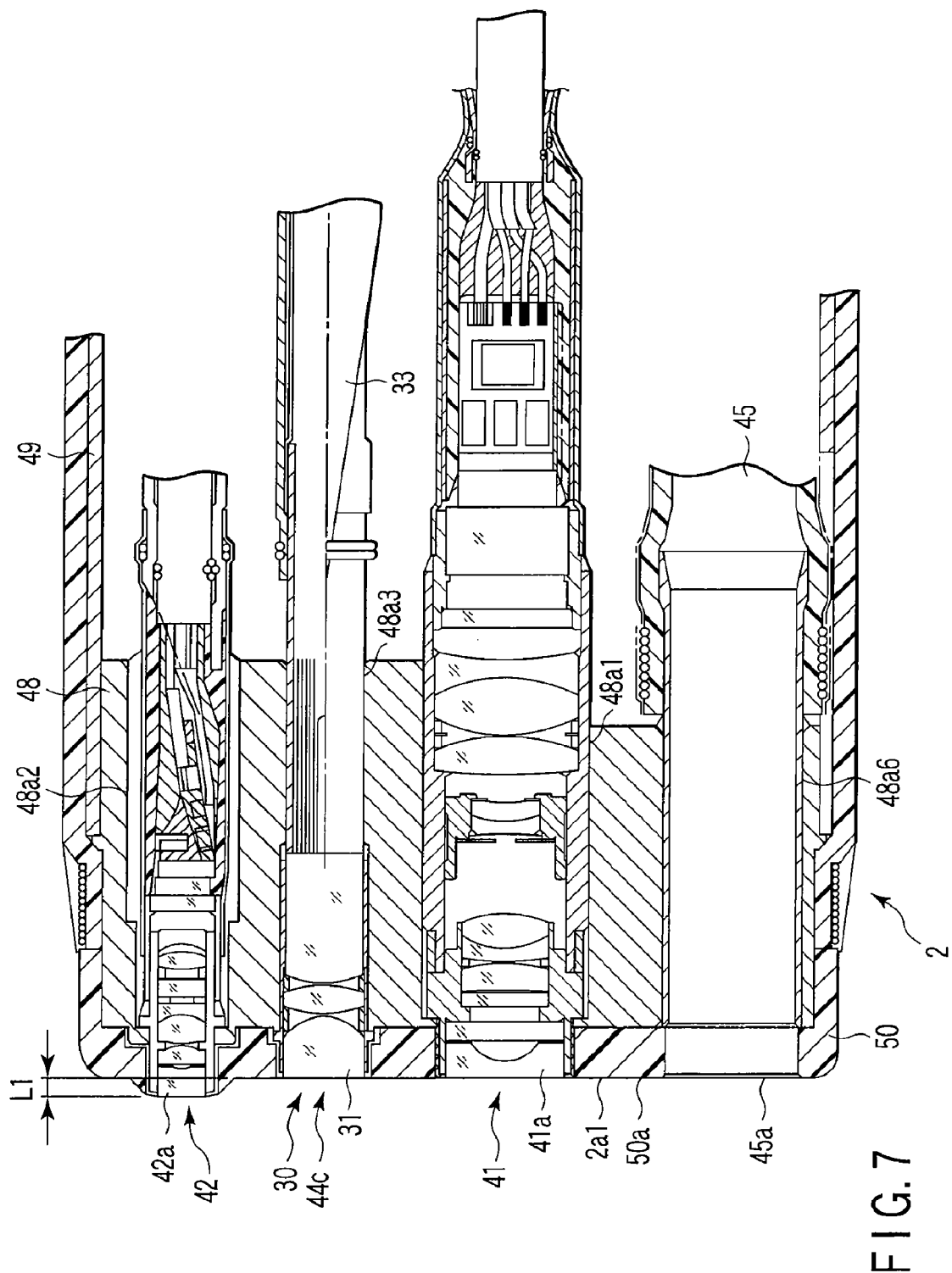
FIG. 7 is a sectional view of the endoscope taken along lines VIIa-VIIb-VIIc-VIId-VIIe-VIIf in FIG. 6.

FIG. 6 and FIG. 7 show a second embodiment of the present invention. The present embodiment has a configuration that the configuration of the distal end portion 2 of the insertion portion 1 of the endoscope according to the first embodiment (see FIG. 1 to FIG. 5A) has been modified in the following manner.

That is, in an endoscope according to the present embodiment, the projecting portion 12 of the first embodiment is not formed on the end face 2a1 of the distal end portion 2 of an insertion portion 1, but the entire end face 2a1 of the distal end portion 2 of the insertion portion 1 is formed to have an approximately smooth flat face, as shown in FIG. 7.

As shown in FIG. 6, an observation optical system of a twin-lens type comprising a first observation portion 41 for ordinary observation observing an area to be examined in a non-contacting state therewith and a second observation portion 42 of an object contact type observing an area to be examined in a contacting state therewith is provided on the end face 2a1 of the distal end portion 2. Further, at least one, three (first, second, and third) in the present embodiment, illumination portions 44A, 44B, and 44C emitting illumination light, a distal end opening 45a of a treatment tool insertion channel (also called "forceps channel") 45, and an opening 46a of a forward water-feeding conduit (forward water-feeding channel) 46 are disposed on the end face 2a1. Incidentally, the first, second, and third illumination portions 44A, 44B, and 44C have an approximately same configuration as those of the first and second illumination portions 4A and 4B of the first embodiment. Therefore, same portions of the present embodiment as those of the first illumination portion 4A are attached with same reference numerals and explanation thereof is here omitted.

FIG. 7 shows an internal configuration of the distal end portion of the insertion portion 1 of the endoscope according to the present embodiment. As shown in FIG. 7, a cylindrical member made from hard metal (distal end hard member) 48 and an annular reinforcing ring 49 fitted on a proximal end side outer peripheral portion of the cylindrical member 48 are disposed within a distal end portion 2 of the insertion portion 1. As shown in FIG. 7, a plurality of, seven (first to seventh) in the present embodiment, hole portions 48a1 to 48a7 (the fifth hole portion 48a5 is not illustrated) parallel to an axial direction of the insertion portion 1 are formed in the cylindrical member 48. A proximal end portion of the reinforcing ring 49 is coupled to a bending piece at a foremost end of a bending portion (not shown).

Further, a distal end cover 50 is attached to a distal end face of the cylindrical member 48 and a distal end side outer peripheral portion of the cylindrical member 48 in a state that it has been fitted on the cylindrical member 48. The distal end cover 50 is formed such that a distal end face 50a thereof orthogonal to an axial direction of the insertion portion 1 entirely has a smooth flat face.

In the present embodiment, a first lens 41a which is an observation lens of the first observation portion 41 for ordinary observation, a first lens 42a which is an observation lens for the second observation portion 42 of an object contact type, and illumination lenses 31 of respective illumination lens units 30 of the three (first, second, and third) illumination portions 44A, 44B, and 44C are disposed on the distal end face 50a of the distal end cover 50, and a distal end opening 45a of a treatment tool insertion channel 45 and an opening 46a of a forward water-feeding conduit 46 are formed thereon.

Further, five (first to fifth) hole portions 48a1 to 48a5 of the cylindrical member 48 of the distal end portion 2 are disposed at sites corresponding to the first observation portion 41, the second observation portion 42, and the first, second, and third illumination portions 44A, 44B, and 44C on the distal end face 50a of the distal end cover 50. Respective constituent elements of the first observation portion 41, respective constituent elements of the second observation portion 42, respective constituent elements of the first illumination portion 44A, respective constituent elements of the second illumination portion 44B, and the respective constituent elements of the third illumination portion 44C are assembled in the first hole portion 48a1, the second hole portion 48a2, the third hole portion 48a3, the fourth hole portion 48a4 (not shown), and the fifth hole portion 48a5 (not shown), respectively.

Further, the remaining two (sixth and seventh) hole portions 48a6 and 48a7 of the cylindrical member 8 are disposed at sites corresponding to the distal end opening 45a of the treatment tool insertion channel 45 and the opening 46a of the forward water-feeding conduit 46 on the distal end face 50a of the distal end cover 50, respectively. Constituent elements of a conduit of the treatment tool insertion channel 45 are coupled to the sixth hole portion 48a6 of the cylindrical member 48. Similarly, constituent elements of the forward water-feeding conduit 46 are coupled to the seventh hole portion 48a7 (not shown) of the cylindrical member 48.

In the present embodiment, a distal end face of the first lens 41a of the first observation portion 41 for ordinary observation and distal end faces of respective illumination lenses 31 of the first to third illumination portions 44A to 44C are disposed to be approximately flush with the distal end face 50a of the distal end cover 50.

On the other hand, fixation is made in a state that the first lens 42a of the second observation portion 42 for object contact type has projected forward from a position of the distal end face 50a of the distal end cover 50 by a proper length L1, for example, about 0.05 mm.

Next, an operation of the present embodiment with the abovementioned configuration will be explained. When a work for inserting the endoscope according to the present embodiment into a body of a patient is performed at a use time of the endoscope, the first observation portion 41 for ordinary observation is used.

Illumination light of, for example, RGB is supplied to the light guide 33 from the light source apparatus in a frame sequential manner and illumination light is emitted in a body cavity of the patient via respective illumination lens 31 of the first to third illumination portions 44A to 44C so that an affected area or the like is illuminated.

A subject such as an affected area illuminated is focused on the light receiving face of an imaging device via the observation optical system of the first observation portion 41 for ordinary observation to be photoelectrically converted. A signal output from the imaging device is input into a signal processing circuit (not shown), and after the signal is processed in the signal processing circuit, color display is performed on a monitor. Thereby, ordinary observation for observing an observation object separated from the first lens 41a of the first observation portion 41 in a wide range is performed using the first observation portion 41 for ordinary observation.

Further, when a site to be examined within a body cavity is contaminated due to adhesion of body fluid or the like thereto, the forward water-feeding button is operated. Body liquid such as sterile water is blown from the opening 46a of the distal end cover 50 of the insertion portion 1 in the insertion direction to the body cavity at an operation time of the forward water-feeding button. Thereby, the body liquid or the like adhering to the site to be examined within the body cavity can be cleaned.

Observation performed by the first observation portion 41 for ordinary observation is continued until the distal end portion 2 of the endoscope inserted into the body of the patient reaches a target observation object site. Switching operation to an observation mode with a high magnification is performed in a state that the distal end portion 2 of the endoscope has approached the target observation object site. Thereby, the observation mode with a high magnification using the second observation portion 42 of an object contact type is switched from the ordinary observation mode performed by the first observation portion 41.

The distal end portion of the first lens 42a of the second observation portion 42 is brought in contact with an object in the state that switching to the observation mode with a high magnification has been performed and object contact observation with a high magnification for observing a cell tissue of an observation object or the like with a high magnification or the like is performed. Incidentally, when magnified observation is performed with a high magnification, for example, pigment is sprayed on an interesting site in advance and the interesting site is dyed so that a contour of the cell can be observed sharply.

The distal end portion 2 of the insertion portion 1 is pressed on a surface of a body tissue H at an observation time of the body tissue H performed by the second observation portion 42 of an object contact type. At this time, the first lens 42a of the second observation portion 42 of an object contact type projecting from the distal end face 50a of the distal end cover 50 is mainly pressed on the surface of the body tissue H. Therefore, the first lens 42a of the second observation portion 42 of an object contact type is brought in contact with the surface of the body tissue H such as a cell tissue of an observation object.

The body tissue H such as a cell tissue is irradiated with illumination light through the respective illumination lenses 31 of the first to third illumination portions 44A to 44C in this state. At this time, a portion of illumination light applied for illumination to the body tissue H such as a cell tissue reaches inside of the body tissue H such as a cell tissue so that it is diffused around abutting faces of the respective illumination lenses 31 of the first to third illumination portions 44A to 44C. Therefore, a surrounding portion of the body tissue H such as a cell tissue ahead of the first lens 42a of the second observation portion 42 of an object contact type is also irradiated with illumination light. Thereby, a portion observed by the first lens 42a of the second observation portion 42 of an object contact type pressed on the surface of the body tissue H such as a cell tissue is also irradiated with illumination light, so that light of the body tissue H such as a cell tissue passes through the first lens 42a of the second observation portion 42 of an object contact type to be focused on the light receiving face of the imaging device and photoelectrically converted. After a signal output from the imaging device is input into a signal processing circuit (not shown) and processed therein, color display is performed on a monitor. Thereby, object contact observation of a high magnification with a high magnification for bringing the first lens 42a of the second observation portion 42 of an object contact type to an observation object to observe a cell tissue of an observation object or the like is performed.

Therefore, the following effects can be achieved in the endoscope with the abovementioned configuration. That is, in the present embodiment, the distal end face of the first lens 41a of the first observation portion 41 for ordinary observation and distal end faces of the respective illumination lenses 31 of the first to third illumination portions 44A to 44C are disposed so as to be approximately flush with the distal end face 50a of the distal end cover 50, and fixation is performed in a state that only the first lens 42a of the second observation portion 42 of an object contact type has projected forward beyond the position of the distal end face 50a of the distal end cover 50 by a proper length L1, for example, about 0.05 mm. Therefore, when the distal end face 50a of the distal end cover 50 of the insertion portion 1 is pressed on an area to be examined at a contact observation time therewith, it is made easy to bring the distal end observation face of the first lens 42a of the second observation portion 42 of an object contact type in contact with a body tissue H of the area to be examined.

Therefore, even if wave, undulation, or the like is formed on a surface H1 of a body tissue H, when the distal end face 50a of the distal end cover 50 of the insertion portion 1 is pressed on the surface H1 of the body tissue H, a gap S1 can be prevented from being formed between the first lens 42a of the second observation portion 42 of an object contact type at the distal end portion 2 of the insertion portion 1 and the surface H1 of the body tissue H. As a result, adverse effect such as flare can be prevented from occurring during cell observation from the observation window due to direct incidence of a portion of illumination light emitted from the first to third illumination portions 44A to 44C on the first lens 42a of the second observation portion 42 of an object contact type.

Incidentally, in the present embodiment, the case that an illumination optical system of an optical fiber system for guiding illumination light to the first to third illumination portions 44A to 44C through the light guide 33 has been used has been shown, but a light source which can be turned ON and OFF by a switch (not shown) such as a light emitting diode (LED) can be used as the light source for the first to third illumination portions 44A to 44C.

Figure 8:
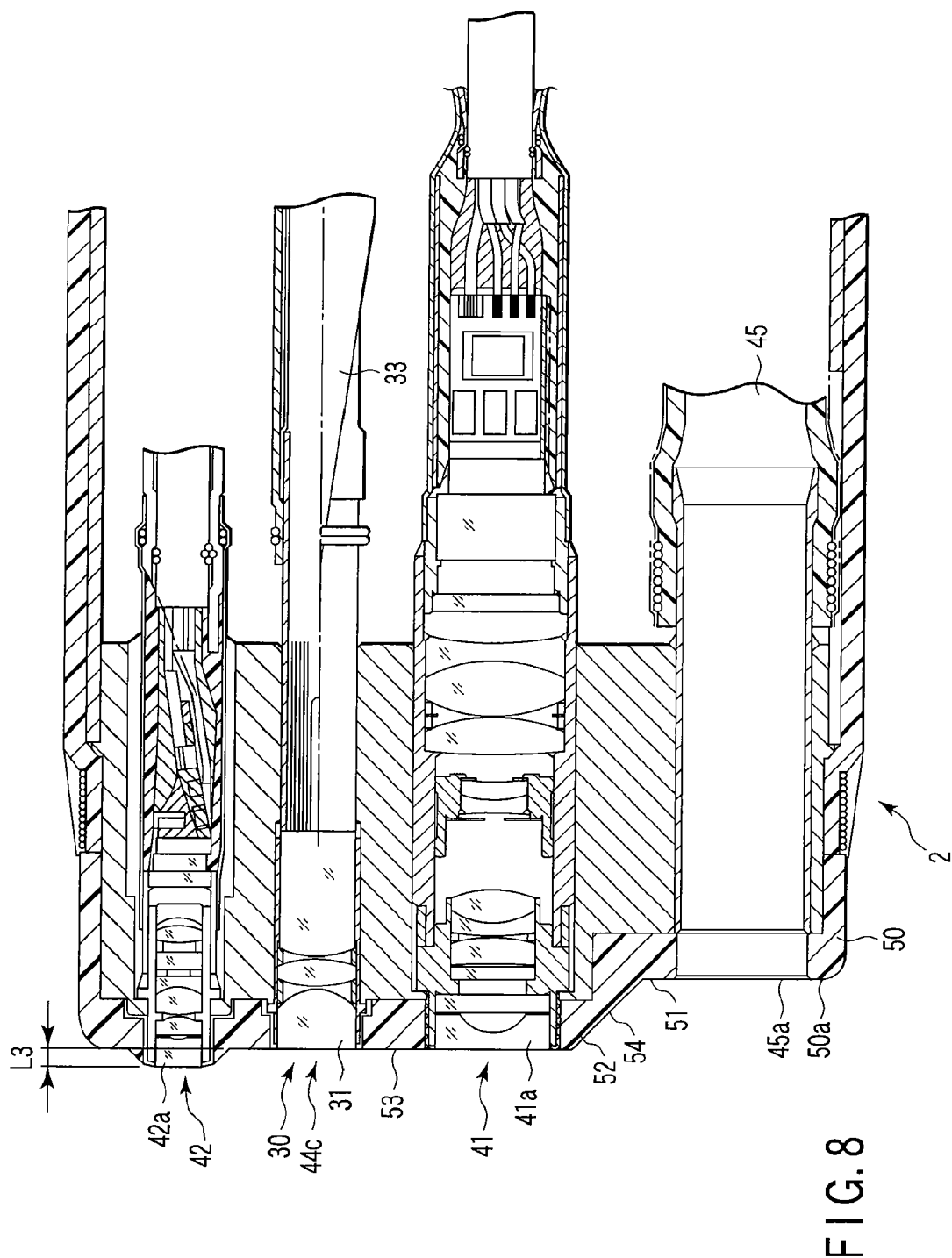
FIG. 8 is a vertical sectional view of a main part showing an internal structure of a distal end portion of an endoscope of a direct view type according to a third embodiment of the present invention.

FIG. 8 shows a third embodiment of the present invention. The present embodiment has such a configuration that the configuration of the distal end portion 2 of the insertion portion 1 of the endoscope having an observation optical system of a twin-lens type having the first observation portion 41 for ordinary observation and the second observation portion 42 for contact observation on the end face 2a1 of the distal end portion 2 of the insertion portion 1 like the second embodiment (see FIG. 6 and FIG. 7) has been modified in the following manner.

That is, in an endoscope according to the present embodiment, as shown in FIG. 8, a flat face-like base face (first face) 51 orthogonal to an axial direction of the insertion portion 1 is formed on the distal end cover 50 disposed on the end face 2a1 of the distal end portion 2 of the insertion portion 1. Further, a projecting portion 52 projecting forward is formed on a portion of the base face. A projecting face (second face) 53 arranged in parallel with the base face 51 is formed on a distal end face of the projecting portion 52. Incidentally, an inclination face 54 with an inclination angle of, for example, about 45° is formed on a wall portion between the base face 51 and the projecting face 53.

In the present embodiment, the projecting face 53 of the projecting portion 52 is formed so as to occupy a circular area of about ¾ of the entire front face of the distal end cover 50, for example. That is, as shown in FIG. 8, an area of about ¼ of the entire circular front face of the distal end cover 50 configures the base face 51.

A first observation portion 41 for ordinary observation for observing an area to be examined in a non-contacting state therewith, a second observation portion 42 of an object contact type for observing an area to be examined in a contacting state therewith, and at least one, three (first, second, and third) in the present embodiment, illumination portions 44A, 44B, and 44C (see FIG. 6) performing irradiation of illumination light are arranged on the projecting face 53 of the projecting portion 52. Further, a distal end opening 45a of a treatment tool insertion channel 45 and an opening 46a (not shown) of a forward water-feeding conduit 46 are disposed on the base face 51.

In the present embodiment, a distal end face of a first lens 41a of the first observation portion 41 for ordinary observation and distal end faces of respective illumination lenses 31 of the first to third illumination portions 44A to 44C are disposed so as to be approximately flush with the projecting face 53 of the projecting portion 52.

On the other hand, fixation is made in a state that a first lens 42a of the second observation portion 42 of an object contact type has projected forward beyond the position of the projecting face 53 of the projecting portion 52 by a proper length L3, for example, about 0.05 mm.

Therefore, the following effects can be achieved in the endoscope with the abovementioned configuration. That is, in the present embodiment, the distal end face of the first lens 41a of the first observation portion 41 for ordinary observation and the distal end faces of the respective illumination lenses 31 of the first to third illumination portions 44A to 44C are disposed so as to be approximately flush with the projecting face 53 of the projecting portion 52, and fixation is made in a state that only the first lens 42a of the second observation portion 42 of an object contact type has projected forward beyond the position of the projecting face 53 of the projecting portion 52 by a proper length L1, for example, about 0.05 mm. Therefore, when the projecting face 53 of the distal end cover 50 of the insertion portion 1 is pressed on an area to be examined at a contact observation time of the area to be examined, it is made easy to bring the distal end observation face of the first lens 42a of the second observation portion 42 of an object contact type in contact with a body tissue H of the area to be examined.

Therefore, even if wave, undulation, or the like is formed on a surface H1 of a body tissue H, when the projecting face 53 of the distal end cover 50 of the insertion portion 1 is pressed on the surface H1 of the body tissue H, a gap S1 can be prevented from being formed between the first lens 42a of the second observation portion 42 of an object contact type at the distal end portion 2 of the insertion portion 1 and the surface H1 of the body tissue H. As a result, like the second embodiment, such an event can be prevented in the present embodiment that a portion of illumination light emitted from the first to third illumination portions 44A to 44C directly enters the first lens 42a of the second observation portion 42 of an object contact type so that adverse effect such as flare occurs during cell observation from the observation window.

Figure 9:
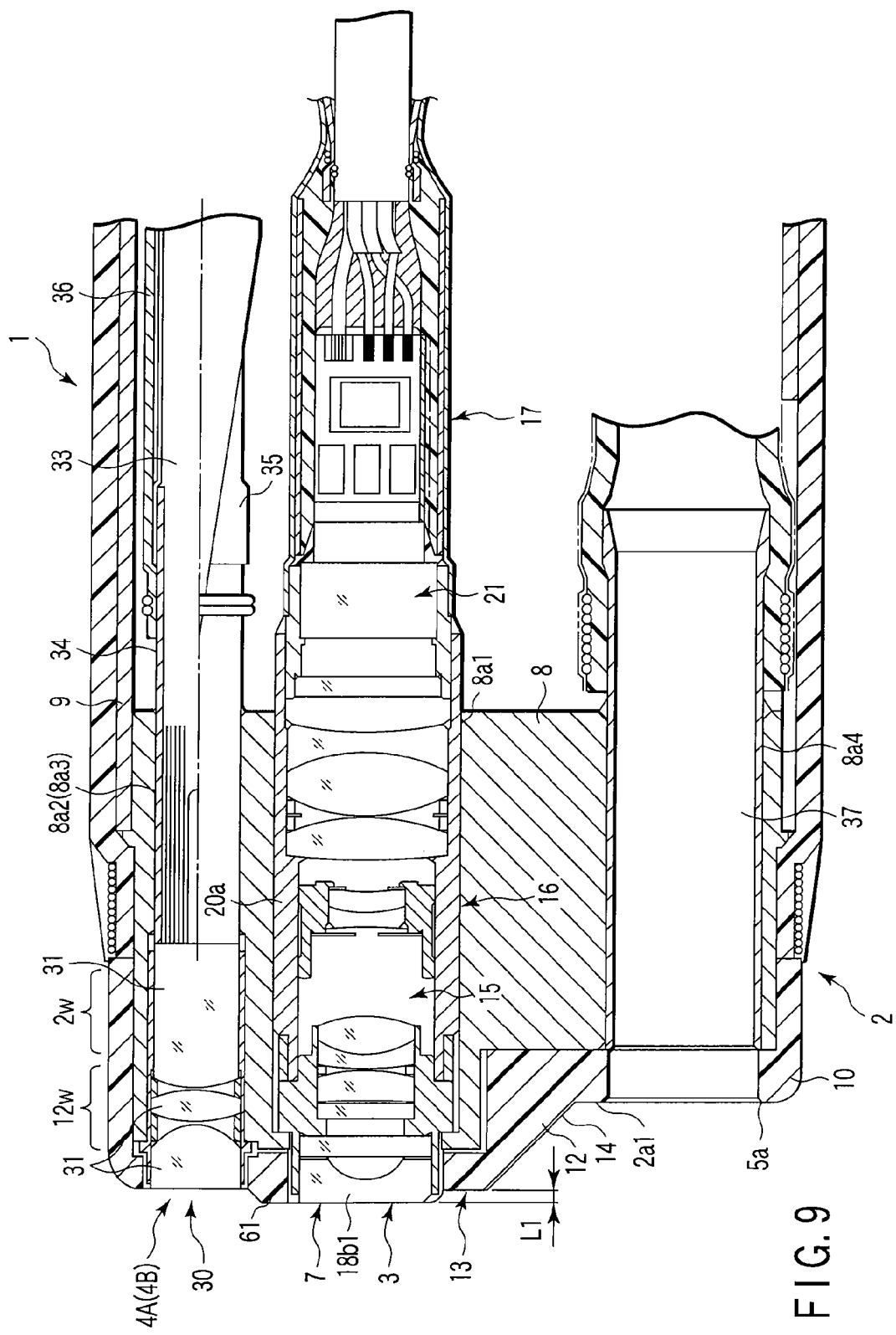
FIG. 9 is a vertical sectional view of a main part showing an internal structure of a distal end portion of an endoscope of a direct view type according to a fourth embodiment of the present invention.

FIG. 9 shows a fourth embodiment of the present invention. The present embodiment has such a configuration that a configuration of the distal end portion 2 of the insertion portion of the endoscope of a single-lens type having an observation optical system 15 of a contact and separation-combined type has been modified like the first embodiment (see FIG. 1 to FIG. 5A) in the following manner. Incidentally, since most part of the present embodiment has the same configuration as that of the first embodiment, same portions in FIG. 9 as those in FIG. 1 to FIG. 5A are attached with same reference numerals and explanation thereof is omitted.

That is, in the endoscope according to the present embodiment, especially as shown in FIG. 9, only an imaging unit of the observation optical system 15 of a contact and separation-combined type projects forward beyond a projecting face 13 of a projecting portion 12 of a distal end cover 10 disposed at the distal end portion 2 of the insertion portion 1 of the endoscope. Here, fixation is performed in a state that a front end portion of a first lens 18b1 of a first unit configuration body 18 has projected forward beyond the position of the projecting face 13 of the projecting portion 12 by a proper length L1, for example, about 0.05 mm.

Further, fixation is performed such that front end portions of the illumination lenses 31 of the first and second illumination portions 4A and 4B are flush with the projecting face 13 of the projecting portion 12. Here, a projecting length L2 of the front end portion of the illumination lens 31 from the projecting face 13 of the projecting portion 12 is 0. The front end portions of the illumination lenses 31 of the first and second illumination portions 4A and 4B are disposed behind the front end portion position of the first lens 18b1 of the first unit configuration body 18 of the observation optical system 15 to satisfy the relationship of L2=0 and L1>0.

A light-shielding wall 61 is formed around the front end portion of the first lens 18b1 of the first unit configuration body 18. The light-shielding wall 61 prevents a portion of illumination light emitted from the illumination lenses 31 of the first and second illumination portions 4A and 4B from directly entering the first lens 18b1 of the observation optical system 15 so that adverse effect such as flare is prevented from being generated during cell observation or ordinary observation (an area to be examined is observed in a non-contact state) from the observation window.

Therefore, the following effects can be achieved in the endoscope with the abovementioned configuration. That is, in the present embodiment, only the first lens 18b1 at the distal end of the observation optical system 15 of contact and separation-combined type projects forward beyond the projecting face 13 of the projecting portion 12 of the distal end cover 10 disposed at the distal end portion 2 of the insertion portion 1 of the endoscope. Therefore, when the projecting face 13 of the projecting portion 12 of the distal end cover 10 of the insertion portion 1 is pressed on an area to be examined in a state that the zoom lens unit 16 of the observation optical system 15 has been switched to the observation mode with a high magnification during contact observation of the area to be examined, it is made easy to bring the distal end observation face of the first lens 18b1 a the distal end of the observation optical system 15 in contact with a body tissue H of the area to be examined.

Therefore, even if wave, undulation, or the like is formed on the surface H1 of the body tissue H, such an event can be prevented that, when the projecting face 13 of the projecting portion 12 of the distal end cover 10 of the insertion portion 1 is pressed on the surface H1 of the body tissue H, a gap S1 is formed between the first lens 18b1 at the distal end of the observation optical system 15 of the distal end portion 2 of the insertion portion 1 and the surface H1 of the body tissue H. As a result, adverse effect such as flare can be prevented from occurring due to direct incidence of a portion of illumination light into the first lens 18b1 at the distal end of the observation optical system 15 during cell observation or ordinary observation (an area to be examined is observed in a non-contact state) from the observation window.

Incidentally, in the present embodiment, the front end portions of the illumination lenses 31 of the first and second illumination portions 4A and 4B are disposed behind the front end portion position of the first lens 18b1 of the first unit configuration body 18 of the observation optical system 15 so that setting is performed so as to satisfy a relationship of L2=0 and L1>0. Therefore, there is a possibility that a portion of illumination light emitted from the illumination lenses 31 directly enters the first lens 18b1 of the observation optical system 15 in the conventional art. There is a possibility that flare occurs in an observation image of the observation optical system 15. However, in the present embodiment, since the light-shielding wall 61 is formed around the distal end portion of the first lens 18b1 of the first unit configuration body 18, a portion of illumination light emitted from the illumination lenses 31 of the first and second illumination portions 4A and 4B can be prevented from directly entering the first lens 18b1 of the observation optical system 15. Therefore, adverse effect such as flare can be prevented from occurring during cell observation from the first lens 18b1 of the observation optical system 15.

FIG. 10 shows a fifth embodiment of the present invention. The present embodiment has such a configuration that a configuration of an endoscope of a single-lens type having an observation optical system 15 of a contact and separation-combined type like the first embodiment (see FIG. 1 to FIG. 5A) has modified in the following manner. Incidentally, since most part of the present embodiment has the same configuration as that of the first embodiment, same portions in FIG. 10 as those in FIG. 1 to FIG. 5A are attached with same reference numerals and explanation thereof is omitted.

That is, in the endoscope according to the present embodiment, especially as shown in FIG. 10, both the first lens 18b1 of the first unit configuration body 18 of the observation optical system 15 of a contact and separation-combined type and the front end portions of illumination lenses 31 of the first and second illumination portions 4A and 4B project forward beyond the projecting face 13 of the projecting portion 12 of the distal end cover 10 disposed at the distal end portion 2 of the insertion portion 1 of the endoscope. Here, fixation is performed in a state that the front end portion of the first lens 18b1 of the first unit configuration body 18 has projected forward beyond the position of the projecting face 13 of the projecting portion 12 by a proper length L1, for example, about 0.05 mm.

Further, setting is performed such that a projecting position L4 of the front end portion of the illumination lenses 31 of the first and second illumination portions 4A and 4B is smaller in projecting amount than the projecting position L1 of the front end portion of the first lens 18b1 of the first unit configuration body 18. Therefore, a relationship of L1>L4>0 is satisfied.

A light-shielding wall 61 similar to that of the fourth embodiment (see FIG. 9) is formed around the front end portion of the first lens 18b1 of the first unit configuration body 18. The light-shielding wall 61 prevents a portion of illumination light emitted from the illumination lenses 31 of the first and second illumination portions 4A and 4B from directly entering the first lens 18b1 of the observation optical system 15, thereby preventing adverse effect such as flare from being generated during cell observation or ordinary observation (an area to be examined is observed in a non-contact state) from the observation window.

Therefore, the following effects can be achieved in the endoscope with the abovementioned configuration. That is, in the present embodiment, both the imaging unit of the observation optical system 15 of a contact and separation-combined type and the front end portions of the illumination lenses 31 of the first and second illumination portions 4A and 4B project forward beyond the projecting face 13 of the projecting portion 12 of the distal end cover 10 disposed at the distal end portion 2 of the insertion portion 1 of the endoscope. Therefore, when the projecting face 13 of the projecting portion 12 of the distal end cover 10 of the insertion portion 1 is pressed on an area to be examined in a state that the zoom lens unit 16 of the observation optical system 15 has been switched to the observation mode with a high magnification at a contact observation time of the area to be examined, it is made easy to bring the distal end observation face of the first lens 18b1 at the distal end of the observation optical system 15 in contact with a body tissue H of the area to be examined.

Therefore, even if wave, undulation, or the like is formed on the surface H1 of the body tissue H, such an event can be prevented that, when the projecting face 13 of the projecting portion 12 of the distal end cover 10 of the insertion portion 1 is pressed on the surface H1 of the body tissue H, a gap S1 is formed between the first lens 18b1 at the distal end of the observation optical system 15 of the distal end portion 2 of the insertion portion 1 and the surface H1 of the body tissue H. As a result, adverse effect such as flare can be prevented from occurring due to direct incidence of a portion of illumination light from the illumination lenses 31 of the first and second illumination portions 4A and 4B into the first lens 18b1 at the distal end of the observation optical system 15 during cell observation or ordinary observation (an area to be examined is observed in a non-contact state) from the observation window.

Further, in the embodiment, especially, setting is performed such that a projecting position L4 of the front end portion of the illumination lenses 31 of the first and second illumination portions 4A and 4B is smaller in projecting amount than a projecting position L1 of the front end portion of the first lens 18b1 of the first unit configuration body 18, so that a relationship of L1>L4>0 is set. Therefore, in the conventional art, there is a possibility that a portion of illumination light emitted from the illumination lenses 31 directly enters the first lens 18b1 of the observation optical system 15 so that there is a possibility that flare occurs in an observation image of the observation optical system 15. However, in the present embodiment, since the light-shielding wall 61 is formed around the front end portion of the first lens 18b1 of the first unit configuration body 18 like the fourth embodiment, a portion of illumination light emitted from the illumination lenses 31 of the first and second illumination portions 4A and 4B can be prevented from directly entering the first lens 18b1 of the observation optical system 15. Therefore, adverse effect such as a flare can be prevented from being generated during cell observation or ordinary observation (an area to be examined is observed in a non-contact state) from the first lens 18b1 of the observation optical system 15.

Figure 11:
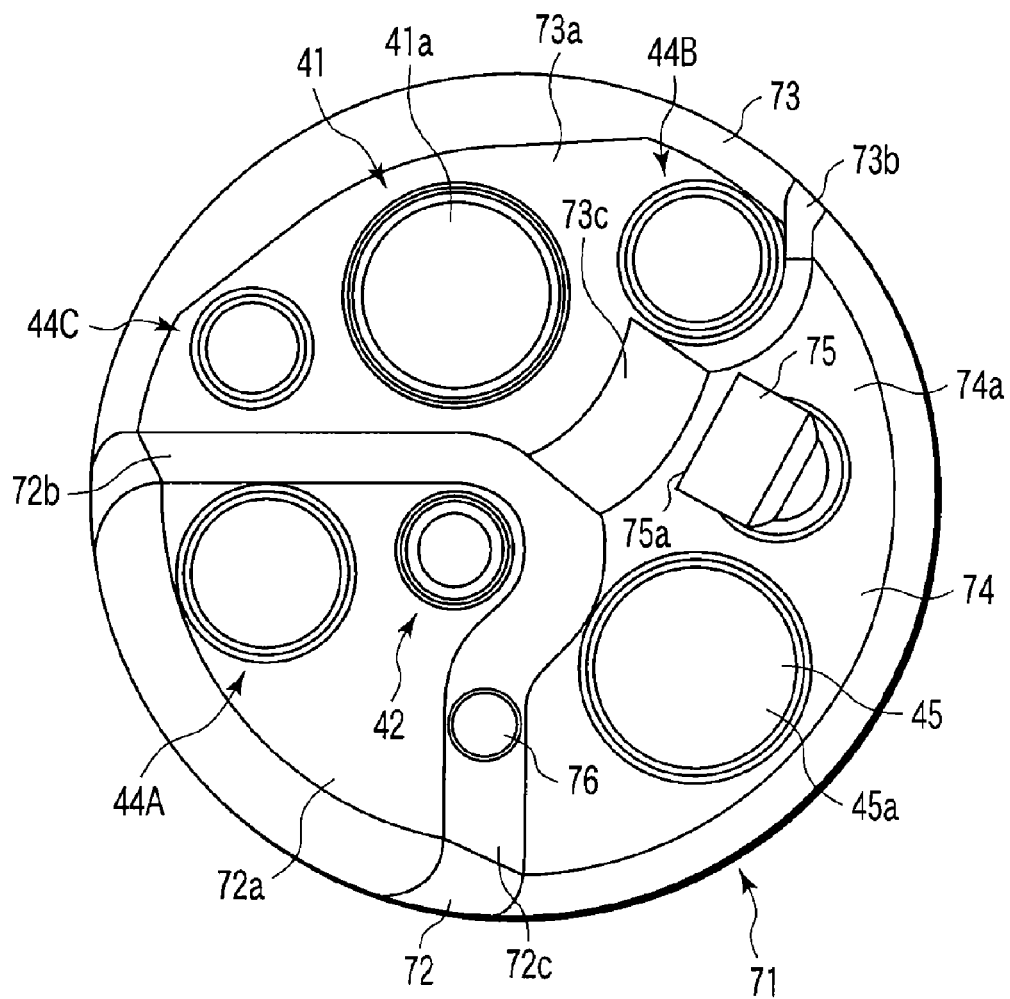
FIG. 11 is a front view showing a distal end portion of an endoscope of a direct view type according to a sixth embodiment of the present invention.
Figure 12:
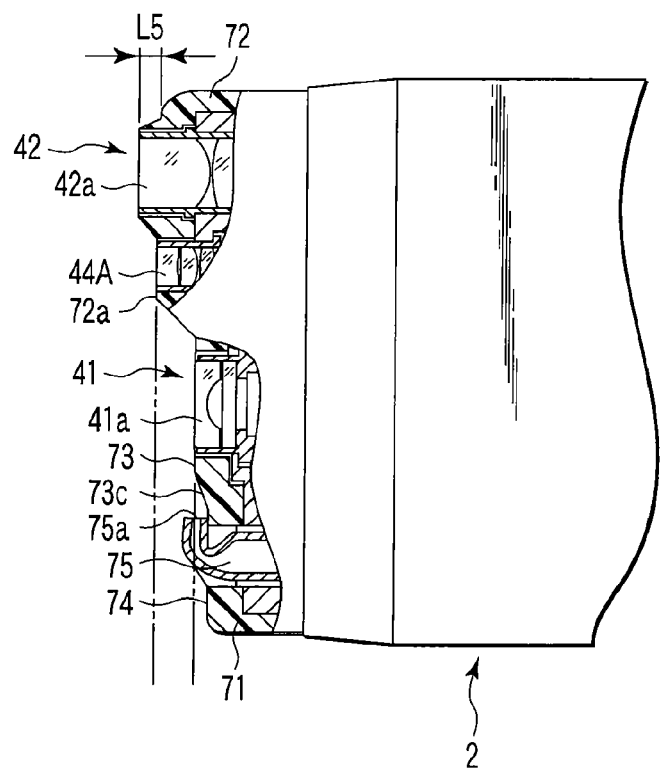
FIG. 12 is a vertical sectional view of a main part showing an internal structure of the distal end portion of the endoscope of a direct view type according to the sixth embodiment.

FIG. 11 and FIG. 12 show a sixth embodiment of the present invention. The present embodiment has such a configuration that a configuration of an endoscope having an observation optical system of a twin-lens type having a first observation portion 41 for ordinary observation and a second observation portion 42 for contact observation on an end face 2a1 of a distal end portion 2 of an insertion portion 1 like the second embodiment (see FIG. 6 and FIG. 7) has been modified in the following manner. Incidentally, since most part of the present embodiment has the same configuration as that of the second embodiment, same portions in FIG. 11 and FIG. 12 as those in FIG. 6 and FIG. 7 are attached with same reference numerals and explanation thereof is omitted.

That is, in the present embodiment, as shown in FIG. 12, three stage step portions 72, 73, and 74 comprising a projecting step portion 72 projecting forward, a middle stage portion 73 lower than the projecting step portion 72 by one step, and a lower stage portion 74 lower than the middle stage portion 73 by one step are formed on a distal end cover 71 disposed at the distal end portion 2 of the insertion portion 1. Here, an end face of the projecting step portion (projecting portion) 72 is formed from a flat face 72a orthogonal to an axial direction of the insertion portion 1. A projecting face is formed from the flat face 72a of the projecting step portion 72.

In the present embodiment, the flat face 72a of the projecting step portion 72 is formed to occupy an area of about ¼ of the entire circular front face of the distal end cover 71. That is, in FIG. 11, the flat face 72a is formed in a region positioned in a lower half of the entire circular front face of the distal end cover 71 and a left side portion regarding a center line extending vertically.

A first lens 41a which is an observation lens of a second observation portion 42 of an object contact type and a first illumination portion 44A are disposed on the flat face 72a of the projecting step portion 72. Here, fixation is made such that the first lens 42a of the second observation portion 42 of an object contact type has projected forward beyond the position of the flat face 72a of the projecting step portion 72 by a proper length L5, for example, about 0.05 mm.

The middle step portion 73 has a flat face 73a approximately parallel to the flat face 72a of the projecting step portion 72. A first lens 41a which is an observation lens of the first observation portion 41 for ordinary observation and two (second and third) illumination portions 44B and 44C are disposed on the flat face 73a of the middle step portion 73. Here, the second and third illumination portions 44B and 44C are disposed on both sides of the first lens 41a of the first observation portion 41. Further, an inclination face 72b with an inclination angle of, for example, about 45' is formed on a wall portion between the middle step portion 73 and the projecting step portion 72.

Incidentally, a step difference between the flat face 72a of the projecting step portion 72 and the flat face 73a of the middle step portion 73 is set to a height which can prevent the projecting step portion 72 from entering a field of view of the first lens 41a of the first observation portion 41, for example, about 0.7 mm.

The lower step portion 74 has a flat face 74a approximately parallel to the flat face 72a of the projecting step portion 72. A distal end opening 45a of a treatment tool insertion channel (also called "forceps channel") disposed within the insertion portion 1 and a gas-feeding/water-feeding nozzle 75 are disposed on the flat face 74a of the lower step portion 74.

Further, an inclination face 73b with an inclination angle of, for example, about 45° and a fluid guide face 73c having an inclination angle smaller than that of the inclination face 73b are formed on a wall portion between the lower step portion 74 and the middle step portion 73. The fluid guide face 73c is disposed between the gas-feeding/water-feeding nozzle 75 of the lower step portion 74 and the first lens 41a of the first observation portion 41 of the middle step portion 73. The fluid guide face 73c is formed from a gentle inclination face with an inclination angle of, for example, about 18°.

A distal end portion of the gas-feeding/water-feeding nozzle 75 is disposed toward the first lens 41a of the first observation portion 41. Further, a jetting port 75a at a distal end opening of the gas-feeding/water-feeding nozzle 75 is disposed so as to face the fluid guide face 73c. Here, as shown in FIG. 12, a distal end face of the jetting port 75a at a distal end opening of the gas-feeding/water-feeding nozzle 75 is disposed so as to be approximately flush with the first lens 41a of the first observation portion 41. Thereby, draining property at a cleaning time can be improved.

A non-projecting face is formed by a portion other than the projecting face which is the flat face 72a of the projecting step portion 72, for example, the flat face 73a of the middle step portion 73, the flat face 74a of the lower step portion 74, the inclination face 72b of the wall portion between the middle step portion 73 and the projecting step portion 72, the inclination face 73b or the fluid guide face 73c on the wall portion between the lower step portion 74 and the middle step portion 73, and the inclination face 72c on the wall portion between the lower step portion 74 and the projecting step portion 72. The inclination face 72c is formed to have an inclination angle of, for example, about 45°.

Here, as shown in FIG. 12, a projecting face which is the flat face 72a of the projecting step portion 72 is disposed forward beyond the distal end portion of the gas-feeding/water-feeding nozzle 75. Thereby, when the flat face 72a of the projecting step portion 72 abuts on an area to be examined, the distal end portion of the gas-feeding/water-feeding nozzle 75 is prevented from being caught by the area to be examined.

Further, an opening 76 for forward water feeding is disposed on the non-projecting face, the inclination face 72c between the lower stage portion 74 and the projecting step portion 72 in the present embodiment, on the distal end portion 2 of the insertion portion 1. The opening 76 communicates with a conduit for forward water feeding (forward water-feeding channel) (not shown) inserted into the insertion portion 1.

Therefore, the following effects can be achieved in the endoscope with the abovementioned configuration.

That is, in the present embodiment, fixation is made in a state that the first lens 42a of the second observation portion 42 of an object contact type has projected forward beyond the position of the flat face 72a of the projecting step portion 72 by a proper length L5, for example, about 0.05 mm. Therefore, when the projecting sep portion 72 of the distal end cover 71 of the insertion portion 1 is pressed on an area to be examined at a contact observation of the area to be examined, it is made easy to bring the distal end observation face of the first lens 42a of the second observation portion 42 of an object contact type in contact with a body tissue H of the area to be examined.

Therefore, even if wave, undulation, or the like is formed on a surface H1 of a body tissue H, when the projecting step portion 72 of the distal end cover 71 of the insertion portion 1 is pressed on the surface H1 of the body tissue H, a gap S1 can be prevented from being formed between the first lens 42a of the second observation portion 42 of an object contact type at the distal end portion 2 of the insertion portion 1 and the surface H1 of the body tissue H. As a result, in the present embodiment, adverse effect such as flare can be prevented from occurring during cell observation from the observation window due to direct incidence of a portion of illumination light emitted from the first to third illumination portions 44A to 44C on the first lens 42a of the second observation portion 42 of an object contact type like the second embodiment.

Figure 13:
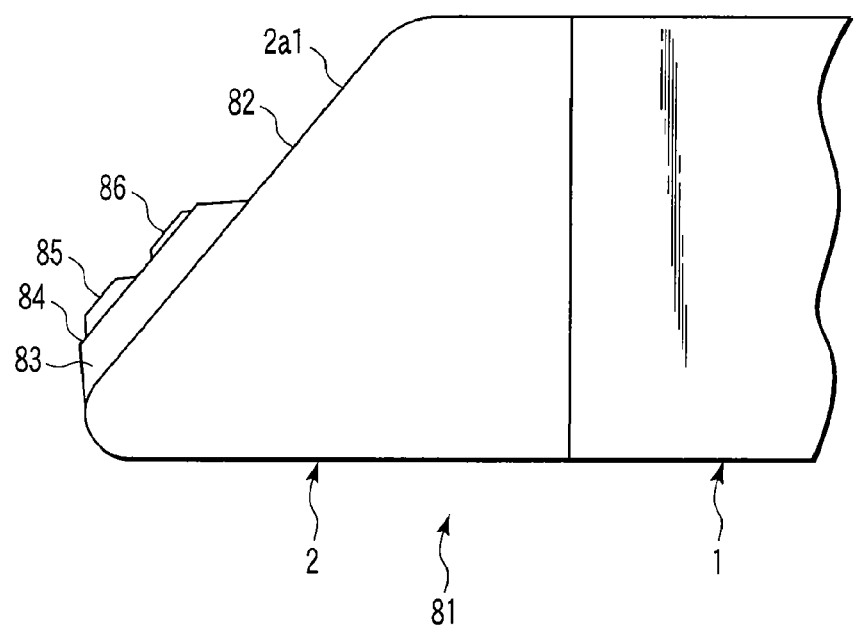
FIG. 13 is a side view showing a distal end portion of an endoscope of an inclination type according to a seventh embodiment of the present invention.

FIG. 13 shows a seventh embodiment of the present invention. The first embodiment (see FIG. 1 to FIG. 5A) has shown the example where the end face 2a1 of the distal end portion 2 of the insertion portion 1 of the endoscope is disposed in a direction orthogonal to the axial line direction of the insertion portion 1 and the present invention is applied to an endoscope of a direct view type performing observation in a forward front face direction, but the present embodiment shows an example that the present invention is applied to an endoscope 81 of an inclination view type where the end face 2a1 of the distal end portion 2 of the insertion portion 1 of the endoscope is formed from an inclination face deviated from a direction orthogonal to the axial line direction of the insertion portion 1. Incidentally, since the remaining portions in the embodiment has the same configuration as those of the endoscope according to the first embodiment, same portions as the endoscope in the first embodiment are attached with same reference numerals and explanation thereof is omitted.

That is, in the endoscope 81 according to the present embodiment, a projecting portion 83 projecting forward from a base face (first face) 82 is formed on the inclination face of the end face 2a1 of the distal end portion 2. A projecting face (second face) 84 disposed in parallel with the base face 82 is formed on a distal end face of the projecting portion 83.

An observation window 85 of an observation optical system of an object contact type with a high magnification observing an area to be examined in a contact state and an illumination portion 86 are disposed on the projecting face 84 of the projecting portion 83. Fixation is made in a state that a first lens of the observation window 85 of an object contact type has projected forward beyond the position of the projecting face 84 of the projecting portion 83 by a proper length.

Therefore, the following effects can be achieved in the endoscope with the abovementioned configuration. That is, in the present embodiment, fixation is made in a state that only the first lens of the observation window 85 of an object contact type has projected forward beyond the position of the projecting face 84 of the projecting portion 83 by a proper length. Therefore, when the projecting face 84 of the distal end portion 2 of the insertion portion 1 is pressed on an area to be examined at a contact observation time of the area to be examined, it can be made easy to bring the distal end observation face of the first lens of the observation window 85 of an object contact type in contact with a body tissue H of the area to be examined.

Therefore, even if wave, undulation, or the like is formed on a surface H1 of a body tissue H, when the projecting face 84 of the distal end portion 2 of the insertion portion 1 is pressed on the surface H1 of the body tissue H, a gap S1 can be prevented from being formed between the first lens of the observation window 85 of an object contact type at the distal end portion 2 of the insertion portion 1 and the surface H1 of the body tissue H. As a result, in the present embodiment, adverse effect such as flare can be prevented from occurring during cell observation from the observation window 85 due to direct incidence of a portion of illumination light emitted from the illumination portion 86 on the first lens of the observation window 85 of an object contact type like the second embodiment.

Incidentally, the present invention is not limited to the abovementioned embodiments. For example, the abovementioned embodiments show the example that the illumination optical system of an optical fiber system for guiding illumination light to the illumination window through the light guide is used, but a light source which can be turned ON and OFF by a switch (not shown), such as a light emitting diode (LED) may be used as the light source for the illumination window. Further, besides, the present invention can be implemented while modified variously without departing from the gist of the present invention, of course.

Next, other characteristic technical items of this application are additionally described as follows:
Note
(Added claim 1) A distal end portion of an endoscope provided with an insertion portion to be inserted into an area to be examined, wherein at least a first face and a second face arranged at a position projecting to a distal end side beyond the first face are provided on a distal end face of the insertion portion, an observation portion for observing the area to be examined and an illumination portion performing irradiation of illumination light are disposed on the second face, and at least a distal end face of an observation window of the observation portion is disposed at a position projecting to a distal end side beyond the second face (Added claim 2) An endoscope wherein a insertion portion distal end face comprises a first face and a second face at a position which has projected to a distal end side beyond the first face, and an observation window whose surface is positioned so as to further project to a distal end side beyond the second face is provided.

(Added claim 3) A contact observation type endoscope where a portion of a distal end portion of the endoscope projects and an observation window with a high magnification is provided on the projecting portion, wherein the observation window further projects beyond a face of the projecting portion.

The present invention is useful in a technical field using an endoscope provided with an observation optical system for ordinary observation and an observation optical system of an object contact type brining a distal end portion of an objective optical system in contact with an object to observe the object, where the endoscope is inserted into a body cavity, or a technical field for manufacturing the endoscope.

What is claimed is:
1. An endoscope comprising
a slender insertion portion having a distal end and a proximal end; and
a distal end face disposed at the distal end of the insertion portion,
where an observation portion for observing an area to be examined and an illumination portion emitting illumination light are disposed on the distal end face, wherein
the observation portion has an observation window on which an observation image of the area to be examined is incident, and
at least a distal end observation face of the observation window is disposed at a position projecting to a distal end side of the insertion portion beyond the distal end face,
wherein the distal end face includes at least a first face, which is a flat base face, a second face, which is a flat face, disposed at a portion projecting to a distal end side of the insertion portion beyond the first face, a third face, which is a flat face, disposed at a portion projecting to the distal end side of the insertion portion beyond the second face, and a fluid guide face disposed between the first face and the second face and is an inclination face inclined from the first face toward the second face,
the observation portion and the illumination portion are disposed on the second face and the third face,
the distal end observation face of the observation window disposed on the third face is disposed so as to project to the distal end side beyond the third face,
the first face, the second face and the third face are configured to be externally exposed when the endoscope is used,
the first face has a gas-feeding/water-feeding nozzle,
the fluid guide face is disposed between the gas-feeding/water-feeding nozzle and the observation portion disposed on the second face in a plan direction of the distal end face,
the gas-feeding/water-feeding nozzle has a jetting port opening toward the fluid guide face and the observation portion disposed on the second face,
the second face projects to the distal end side of the insertion portion beyond the jetting port, and
the third face projects to the distal end side of the insertion portion beyond the gas-feeding nozzle.
2. The endoscope according to claim 1, wherein
the distal end face of the insertion portion is formed from an inclination face deviated from a direction orthogonal to an axial line direction of the insertion portion.
3. The endoscope according to claim 1, wherein
the distal end face includes at least a first face and a second face disposed at a portion projecting to a distal end side of the insertion portion beyond the first face,
the observation portion and the illumination portion are disposed on the second face, and
at least the distal end observation face of the observation window is disposed so as to project to the distal end side beyond the second face.
4. The endoscope according to claim 3, wherein
the observation portion includes a first observation portion observing the area to be examined in a non-contact state therewith and
a second observation portion observing the area to be examined in a contact state therewith, and
at least the second observation portion is disposed on the second face.
5. The endoscope according to claim 4, wherein
the second observation portion has an observation optical system with a magnification higher than that of the first observation portion.

* * * * *